(12) United States Patent
Martin et al.

(10) Patent No.: US 8,110,538 B2
(45) Date of Patent: Feb. 7, 2012

(54) PERACID/PEROXIDE COMPOSITION AND USE THEREOF AS AN ANTI-MICROBIAL AND A PHOTOSENSITIZER

(75) Inventors: Charles W. Martin, Ellisville, MO (US); Joan A. Stader, Ballwin, MO (US); Jeffry Golden, Creve Coeur, MO (US)

(73) Assignee: BioMed Protect, LLC, St. Louis, MO (US)

( * ) Notice: Subject to any disclaimer, the term of this patent is extended or adjusted under 35 U.S.C. 154(b) by 925 days.

(21) Appl. No.: 11/329,433

(22) Filed: Jan. 11, 2006

(65) Prior Publication Data

US 2006/0229225 A1    Oct. 12, 2006

Related U.S. Application Data

(60) Provisional application No. 60/642,819, filed on Jan. 11, 2005.

(51) Int. Cl.
C11D 1/34 (2006.01)
C11D 3/26 (2006.01)
C11D 3/37 (2006.01)

(52) U.S. Cl. ........ 510/383; 510/161; 510/191; 510/238; 510/372; 510/423; 510/467; 510/500; 510/505; 422/28; 134/39; 134/42

(58) Field of Classification Search .......... 510/161, 510/191, 238, 372, 383, 423, 467, 500, 505; 422/28; 134/39, 42
See application file for complete search history.

(56) References Cited

U.S. PATENT DOCUMENTS

| | | | |
|---|---|---|---|
| 2,284,477 A | 5/1942 | Reichert et al. |
| 2,814,641 A | 11/1957 | Phillips et al. |
| 3,679,587 A | 7/1972 | Smith et al. |
| 3,988,318 A | 10/1976 | Copes |
| 4,051,058 A | 9/1977 | Bowing et al. |
| 4,051,059 A | 9/1977 | Bowing et al. |
| 4,404,191 A | 9/1983 | Sporkenbach et al. |
| 4,477,438 A | 10/1984 | Willcockson et al. |
| 4,557,898 A | 12/1985 | Greene et al. |
| 4,743,447 A | 5/1988 | Le Rouzic et al. |
| 4,783,194 A | 11/1988 | Dugenet et al. |
| 4,915,863 A | 4/1990 | Aoyagi et al. |
| 5,008,079 A | 4/1991 | Wutzler et al. |
| 5,077,008 A | 12/1991 | Kralovic et al. |
| 5,078,896 A | 1/1992 | Rorig et al. |
| 5,294,644 A | 3/1994 | Login |

(Continued)

FOREIGN PATENT DOCUMENTS

WO    WO 80/01457    7/1980

(Continued)

OTHER PUBLICATIONS

Bayliss, C.E. et al., "The Combined Effect of Hydrogen Peroxide and Ultraviolet Irradiation on Bacterial Spores", *Journal of Applied Bacteriology*, vol. 47, pp. 263-269.

(Continued)

*Primary Examiner* — Gregory Delcotto
(74) *Attorney, Agent, or Firm* — Thomas, Kayden, Horstemeyer & Risley, LLP

(57) ABSTRACT

A microbicidal and decontaminant composition comprising an aqueous solution of peroxides and peracids having equilibrium reaction products, a photoreactive surfactant, and a polymer, wherein said polymer interacts with said peroxides and said peracids.

32 Claims, 24 Drawing Sheets

U.S. PATENT DOCUMENTS

| | | | |
|---|---|---|---|
| 5,298,529 A | 3/1994 | Narayanan | |
| 5,344,652 A | 9/1994 | Hall, II et al. | |
| 5,349,083 A | 9/1994 | Brougham et al. | |
| 5,350,563 A | 9/1994 | Kralovic et al. | |
| 5,435,939 A | 7/1995 | Narayanan | |
| 5,437,868 A | 8/1995 | Oakes et al. | |
| 5,489,434 A | 2/1996 | Oakes et al. | |
| 5,508,046 A | 4/1996 | Cosentino et al. | |
| 5,516,486 A | 5/1996 | Wright et al. | |
| 5,534,435 A | 7/1996 | Godtfredsen et al. | |
| 5,545,374 A | 8/1996 | French et al. | |
| 5,565,231 A | 10/1996 | Malone et al. | |
| 5,624,634 A | 4/1997 | Brougham et al. | |
| 5,632,676 A | 5/1997 | Kuschner et al. | |
| 5,656,302 A | 8/1997 | Cosentino et al. | |
| 5,696,046 A | 12/1997 | Green | |
| 5,718,910 A | 2/1998 | Oakes et al. | |
| 5,720,983 A | 2/1998 | Malone | |
| 5,756,139 A | 5/1998 | Harvey et al. | |
| 5,900,256 A | 5/1999 | Scoville, Jr. et al. | |
| 5,914,303 A | 6/1999 | Sankey et al. | |
| 6,008,405 A | 12/1999 | Gray et al. | |
| 6,010,993 A | 1/2000 | Romano et al. | |
| 6,015,832 A | 1/2000 | Baker, Jr. et al. | |
| 6,028,104 A | 2/2000 | Schmidt et al. | |
| 6,036,918 A | 3/2000 | Kowando | |
| 6,096,348 A | 8/2000 | Miner et al. | |
| 6,096,349 A | 8/2000 | Petri et al. | |
| 6,103,683 A | 8/2000 | Romano et al. | |
| 6,106,854 A | 8/2000 | Belfer et al. | |
| 6,121,219 A | 9/2000 | Herdt et al. | |
| 6,143,088 A | 11/2000 | Lion | |
| 6,165,483 A | 12/2000 | Hei et al. | |
| 6,168,808 B1 | 1/2001 | Hamon Godin et al. | |
| 6,183,807 B1 | 2/2001 | Gutzmann et al. | |
| 6,207,108 B1 | 3/2001 | Carr et al. | |
| 6,238,685 B1 | 5/2001 | Hei et al. | |
| 6,245,957 B1 | 6/2001 | Wagner et al. | |
| 6,274,542 B1 | 8/2001 | Carr et al. | |
| 6,342,528 B1 | 1/2002 | McKenzie et al. | |
| 6,369,288 B1 | 4/2002 | Brown | |
| 6,399,557 B2 * | 6/2002 | Perkins et al. | 510/310 |
| 6,403,547 B1 | 6/2002 | Grippaudo et al. | |
| 6,436,445 B1 | 8/2002 | Hei et al. | |
| 6,444,634 B1 | 9/2002 | Mason et al. | |
| 6,462,008 B1 | 10/2002 | Ortiz | |
| 6,472,360 B1 | 10/2002 | Beggs et al. | |
| 6,479,454 B1 | 11/2002 | Smith et al. | |
| 6,489,281 B1 | 12/2002 | Smith et al. | |
| 6,514,556 B2 | 2/2003 | Hilgren et al. | |
| 6,518,307 B2 | 2/2003 | McKenzie et al. | |
| 6,521,661 B1 | 2/2003 | Chen et al. | |
| 6,525,237 B1 | 2/2003 | Purdon | |
| 6,527,872 B1 | 3/2003 | Fricker et al. | |
| 6,530,384 B1 | 3/2003 | Meyers et al. | |
| 6,545,047 B2 | 4/2003 | Gutzmann et al. | |
| 6,566,574 B1 | 5/2003 | Tadros et al. | |
| 6,627,593 B2 | 9/2003 | Hei et al. | |
| 6,692,694 B1 | 2/2004 | Curry et al. | |
| 6,699,433 B2 | 3/2004 | Weinberg et al. | |
| 6,723,890 B2 | 4/2004 | Tucker et al. | |
| 2004/0002434 A1 * | 1/2004 | Perkins et al. | 510/309 |
| 2004/0038843 A1 * | 2/2004 | Busch et al. | 510/311 |

FOREIGN PATENT DOCUMENTS

WO  WO 98/43879  10/1998

OTHER PUBLICATIONS

Bayliss, C.E. et al., "The Effect of Hydrogen Peroxide and Ultraviolet Irradiation on Non-Sporing Bacteria", *Journal of Applied Bacteriology*, vol. 48, pp. 417-422.

Bayliss, C.E. et al., "Resistance and Structure of Spores of *Bacillus subtilis*", *Journal of Applied Bacteriology*, vol. 50, pp. 379-390.

Prototype Field Test Report: Electrostatic Decontamination for CB Counter-Terrorism, Clean Earth Technologies, 2003.

Halliwell, B. et al., "Free Radicals in Biology and Medicine", *Oxford University Press*, New York, 2000, pp. 53-55.

Strauss, J.H. et al., "Purification and Properties of Bacteriophage MS2 and of its Ribonucleic Acid", *Journal of Molecular Biology*, 1963, vol. 7, pp. 43-54.

Hussaini, S.N. et al., "Sporicidal Activity of Peracetic Acid Against *B. anthracis* Spores", *The Veterinary Record*, 1976, pps. 257-259.

Kline, L.B. et al., "The Virucidal Properties of Peracetic Acid", *Amer. Journal of Clinical Pathology*, 1960, vol. 33, pp. 30-33.

Lenahan, R.J. "Peroxyacetic Acid: The New Generation Santizier", *MBAA Technical Quarterly*, 1992, vol. 29, pp. 53-56.

Mottishaw, J. et al., "The Resistance of Bacterial Spores to Peracetic Acid and Peracetic Acid/Other Chemical Mixtures", *Campden Food Preservation Research Association*, 1982, pp. 1-85.

Bailey, G.F. et al., Ultraviolet-Absorption Spectra of Dry Bacterial Spores, *Journal of Bacteriology*, 1965, vol. 89[4], pp. 984-987.

McDonnell, G. et al., "Antiseptics and Disinfectants: Activity, Action, and Resistance", *J. Clin. Microbiol.*, 1999, Rev. 12, pp. 147-179.

Sagripanti, J.L. et al., "Bacterial Spores Survive Treatment with Commercial Sterilants and Disinfectants", *Appl. Environ. Microbiol.*, 1999, vol. 65, pp. 4255-4260.

Springthorpe, V.S. et al., "Chemical Disinfection of Virus-Contaminated Surfaces", *Critical Reviews in Environment Control*, 1990, vol. 20, pp. 169-229.

Wheat, P.F., "History and Development of Antimicrobial Susceptibility Testing Methodology", *Journal of Antimicrobial Chemotherapy*, 2001, vol. 48, pp. 1-4.

Bank, H.L. et al., "Bactericidal Effectiveness of Modulated UV Light", *Applied and Environmental Microbiology*, 1990, vol. 56 [12], pp. 3888-3889.

Zelle, M.R. et al., "Effects of Radiation on Bacteria", *Radiation Biology*, 1955, pp. 365-430.

Block, S.S., "Disinfection, Sterilization, and Preservation", *Lippincott, Williams, & Wilkins*, 2001, Ch. 9, Peroxygen Compounds.

Tan, Y.T.F. et al., "Investigation of Interpolymer Complexation Between Carbopol and Various Grades of PVP and Effects on Adhesion Strength and Swelling Properties", *J. Pharm. Pharmaceut. Sci.*, 2001, vol. 4, pp. 7-14.

Myers, D. "Surfaces, Interfaces and Colloids: Principles and Applications", *Wiley-VCH*, 1999, pp. 347-348.

\* cited by examiner

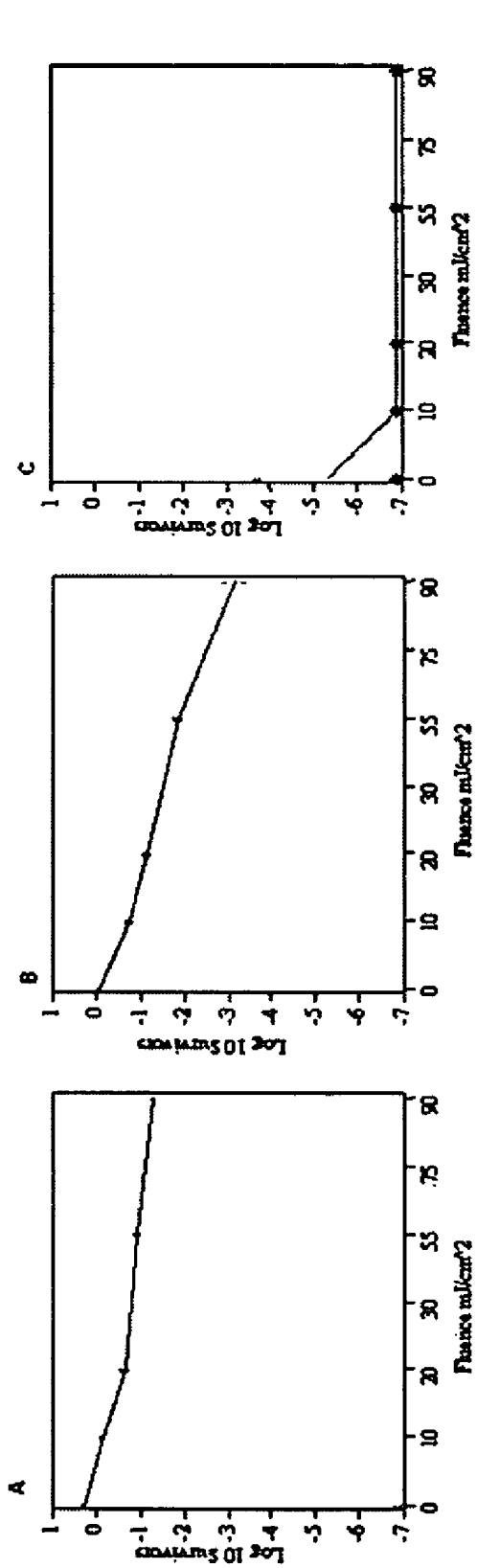

PERACID/PEROXIDE COMPOSITION AND USE THEREOF AS AN ANTI-MICROBIAL AND A PHOTOSENSITIZER

CROSS REFERENCE TO RELATED APPLICATIONS

This application claims the benefit of U.S. Provisional Application No. 60/642,819 filed Jan. 11, 2005 and the disclosure is incorporated herein by reference.

FIELD OF THE INVENTION

The present invention is in the field of peracid- and peroxide-containing compositions for decontamination, disinfection and microbicidal treatment. This field includes formulations for use as sanitizers, disinfectants, sterilants/sporicides, and fungicides/moldicides and includes anti-microbial compositions that are solutions, aerosols, and vapors. Among such compositions are those that may be used as photosensitizers, which when used in combination with light result in greater efficacy or a faster rate of treatment.

BACKGROUND OF THE INVENTION

Compositions for decontamination, disinfection and sterilization must have excellent microbicidal efficacy (ME) and be non-corrosive. It is also generally desirable that the composition act rapidly. For the treatment of objects and surfaces, it is further desirable that good ME be achieved with minimal quantities of the composition. For surfaces, this means the application volume is relatively low, i.e., a small volume covers a large surface. In addition, the use of compositions that act with a variety of microbicidal mechanisms offers less likelihood of leading to the evolution of organisms that are resistant to disinfection. Decontaminant, disinfectant and sterilant compositions that act with 'dark' chemistry and also with light-activated 'photochemistry' offer such multiple 'kill' mechanisms.

Spores are generally regarded as more difficult to kill than vegetative bacteria and viruses. However, because of their smaller size, viruses can be located in pores and crevices and thereby evade contact with decontaminants, disinfectants and sterilants, which do not penetrate well into such spaces. Moreover, the wetting of the microbe to be killed by the decontaminant, disinfectant or sterilant aids the mass-transfer and contact of the lethal chemical species with the target loci of the microbe and its biochemical components. Thus, another key attribute of the disinfectant and/or sterilant is that it has good rheological properties. Such properties affect the application of the composition and also its ME.

Compositions containing peroxide, especially hydrogen peroxide (HP), and one or more peracids, especially peracetic acid (also called peroxyacetic acid, PAA) have been proven to be very effective sporicides, bactericides, and virucides. Many such preparations have passed the necessary tests and are registered products as sanitizers, disinfectants, and sporicides. A few are also products registered as sterilants. Many of these peroxide/peracid compositions are liquid solutions, which can be used for treating aqueous solutions, surfaces and objects. Some are approved for food contact surfaces and for sanitization of some food products. Some are also registered as disinfectants or sterilants as vapor phase treatments. Examples of such products, methods for their use and descriptions of the mechanisms whereby they kill microbes are found extensively in the scientific literature and in the patented prior art.

While PAA is known to be an effective sporicide and virucide, it is also corrosive and a strong oxidizer and it can be hazardous to handle. HP is effective as a bactericide and virucide; however, it is also a strong oxidizer. Accordingly, such highly reactive materials are also difficult to store for long periods of time, e.g., many months or years. Trace amounts of impurities, especially metals, can react with the HP and the PAA and cause decomposition. Therefore, many peroxide/peracid compositions include anti-corrosive and stabilizing ingredients. In many examples, these are surfactants that coat surfaces, or that sequester metals and metal-containing impurity materials. Because HP and PAA have an equilibrium reaction that includes acetic acid, the use of buffering materials and the addition of acetic acid to such compositions is commonplace.

Some of the peroxide and peroxide/peracid containing compositions are also known to act as photosensitizers. The application of such compositions onto a surface or object, or as an aerosol cloud, followed by illumination, especially by an intense ultraviolet (UV) light, can result in very rapid microbicidal action, as has been described in the prior art. Also described are commercial products that have been found to be photosensitizers. Two examples are Zerotol™ and Rennalin™. Still others are mixtures of peroxycarboxylic acids.

Photosensitized decontamination, disinfection and sterilization offer rapid treatment, may permit a low application volume of the composition (which means lower logistical requirements for the treatment), and multiple kill mechanisms.

In spite of more than a half century of development of peroxide and peracid compositions, the prior art does not describe compositions that have outstanding ME, very low corrosivity, compatibility with a large variety of materials to be disinfected or sterilized, and that are excellent for use in photosensitized decontamination or disinfection with concomitant irreversible nucleic acid destruction or sterilization.

The object of the present invention is a peroxide/peracid composition that solves one or more of the above-identified problems.

DESCRIPTION OF THE FIGURES

FIG. 3. Applying Challenge Organisms to Panels. The application process is described in the text.

FIG. 7 ME as a function of the UV light fluence for treatment of *Bacillus globigii* (Bg, also called *Bacillus atro-*

*phaeus*) spores. Shown is a comparison of results for treatment by (FIG. 7A) UV only, (FIG. 7B) 4% HP plus V, and (FIG. 7C) 4% BDS plus UV. Challenge level was $1\times10^8$ Bg spores ($8\times10^4$ Bg spores/mm$^2$). Very high level kill is seen in FIG. 7C. The asterisk (*) denotes the level of detection (~7 logs) where no colonies were produced.

Figures 8A, 8B, 8C:
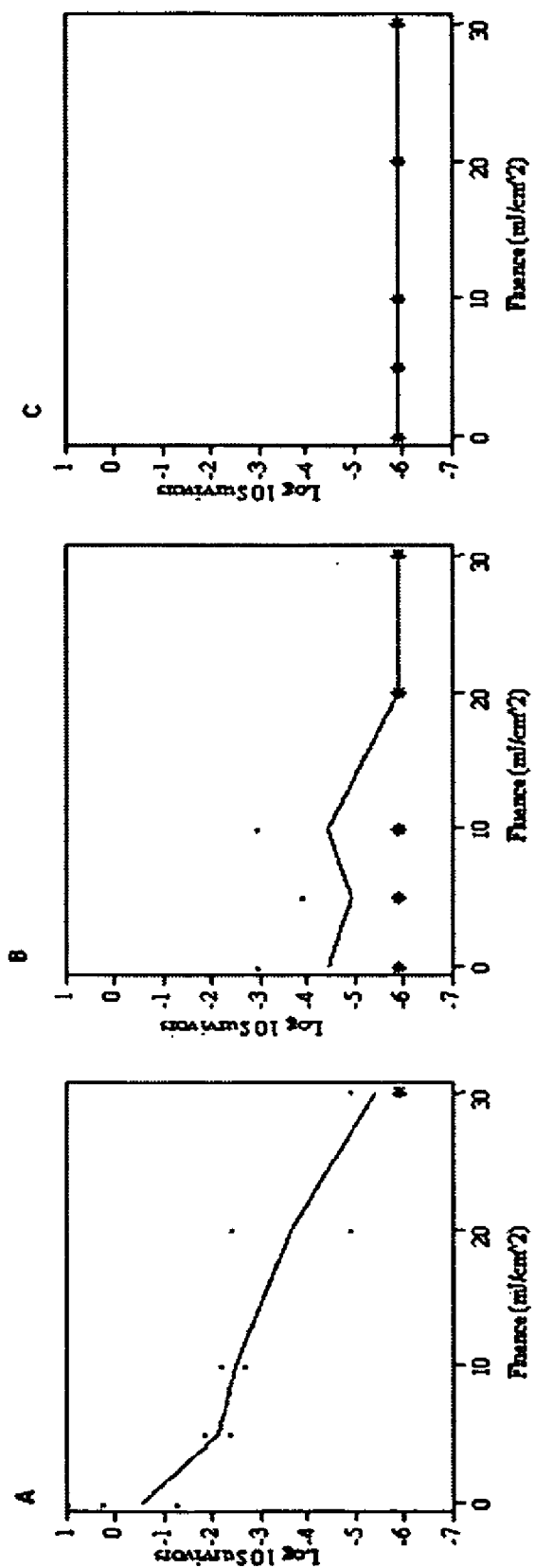

FIG. 8. ME as a function of the UV light fluence for treatment of *E. coli* cells by (FIG. 8A) UV Only, (FIG. 8B) 4% HP plus V, and (FIG. 8C) 4% BDS plus UV (the EDS process). BDS and the EDS process kill to the level of detection. The challenge level was $1\times10^8$ CFU ($8\times10^4$ CFU/mm$^2$). The asterisk (*) denotes the level of detection where no colonies were produced.

FIG. 9. Comparison of microbicidal efficacy for treatment with and without high UV content light, as a function of BDS concentration.

Figure 10:
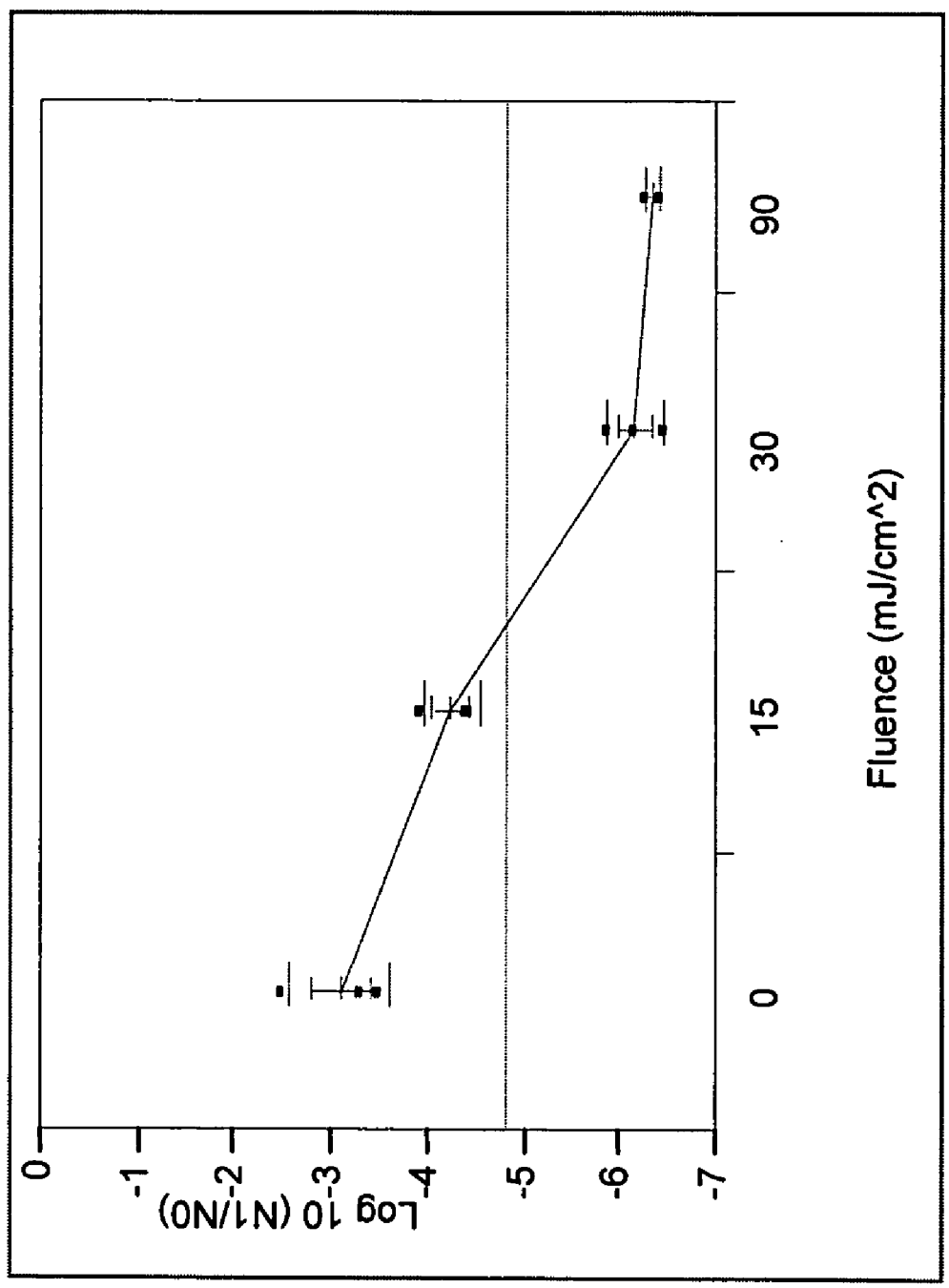

FIG. 10. Microbicidal efficacy of 4% BDS plus UV light (EDS process) of *Bacillus anthracis* (Ba) spores.

Figure 11:
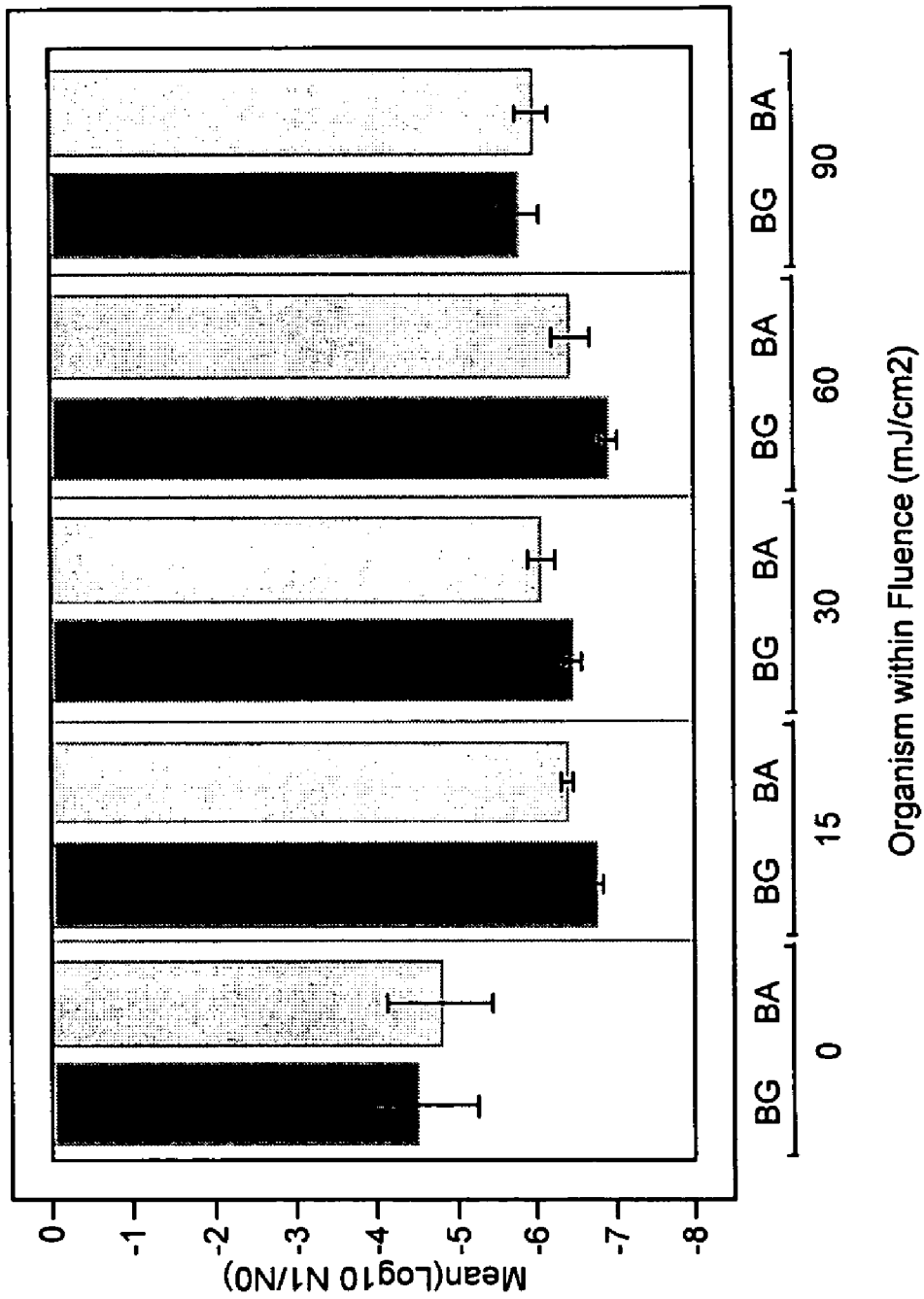

FIG. 11. Correlation of the ME for Bg and Ba spores prepared by identical methodology. The growth medium for both strains was Schaeffer's sporulation medium.

Figure 12:
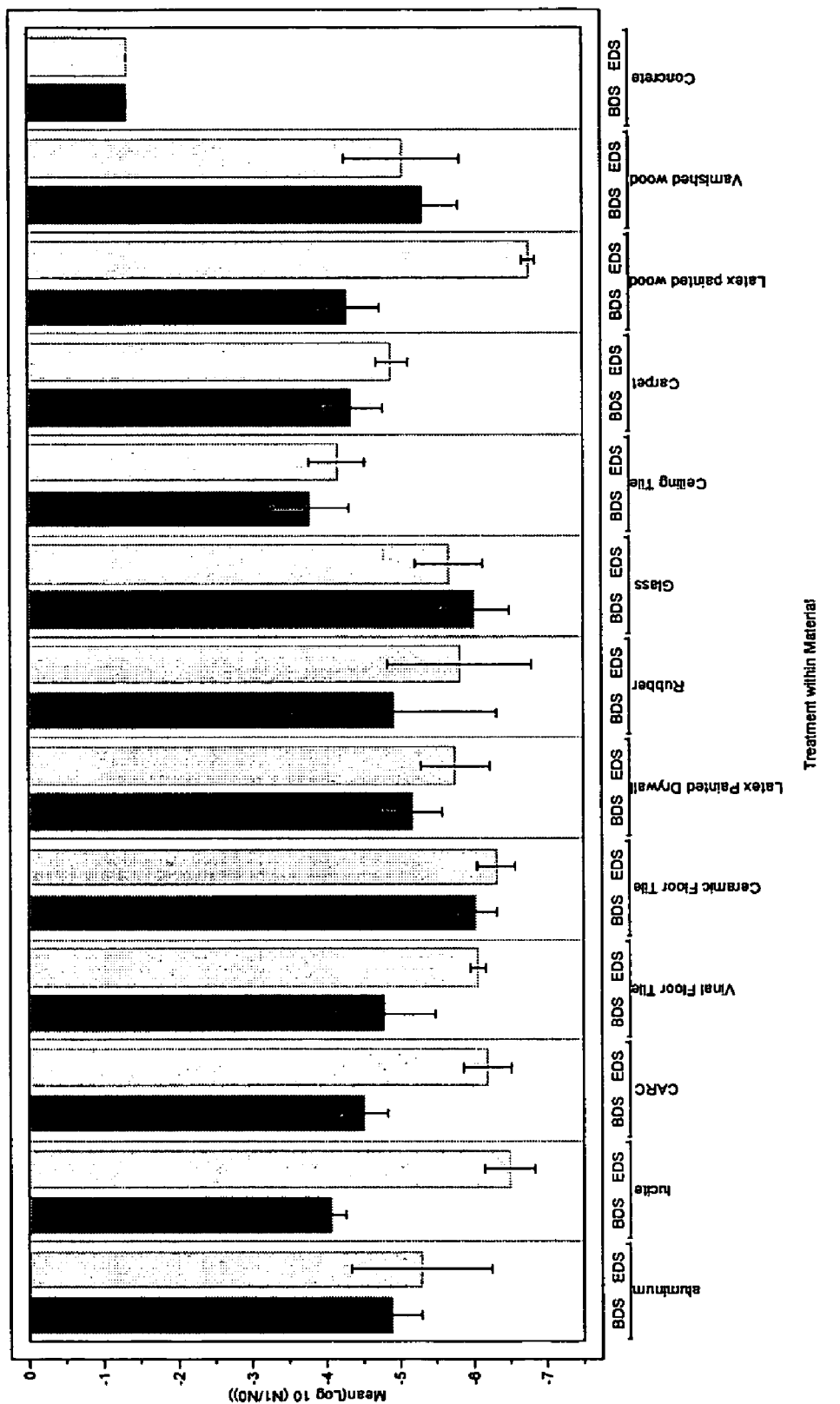

FIG. 12. Shown is the comparison of sporicidal ME for treatment by the BDS as a photosensitizer plus light with high UV content (the EDS treatment process), and disinfection by treatment with BDS alone (labeled 'BDS') on one foot square panels of various materials.

Figure 13:
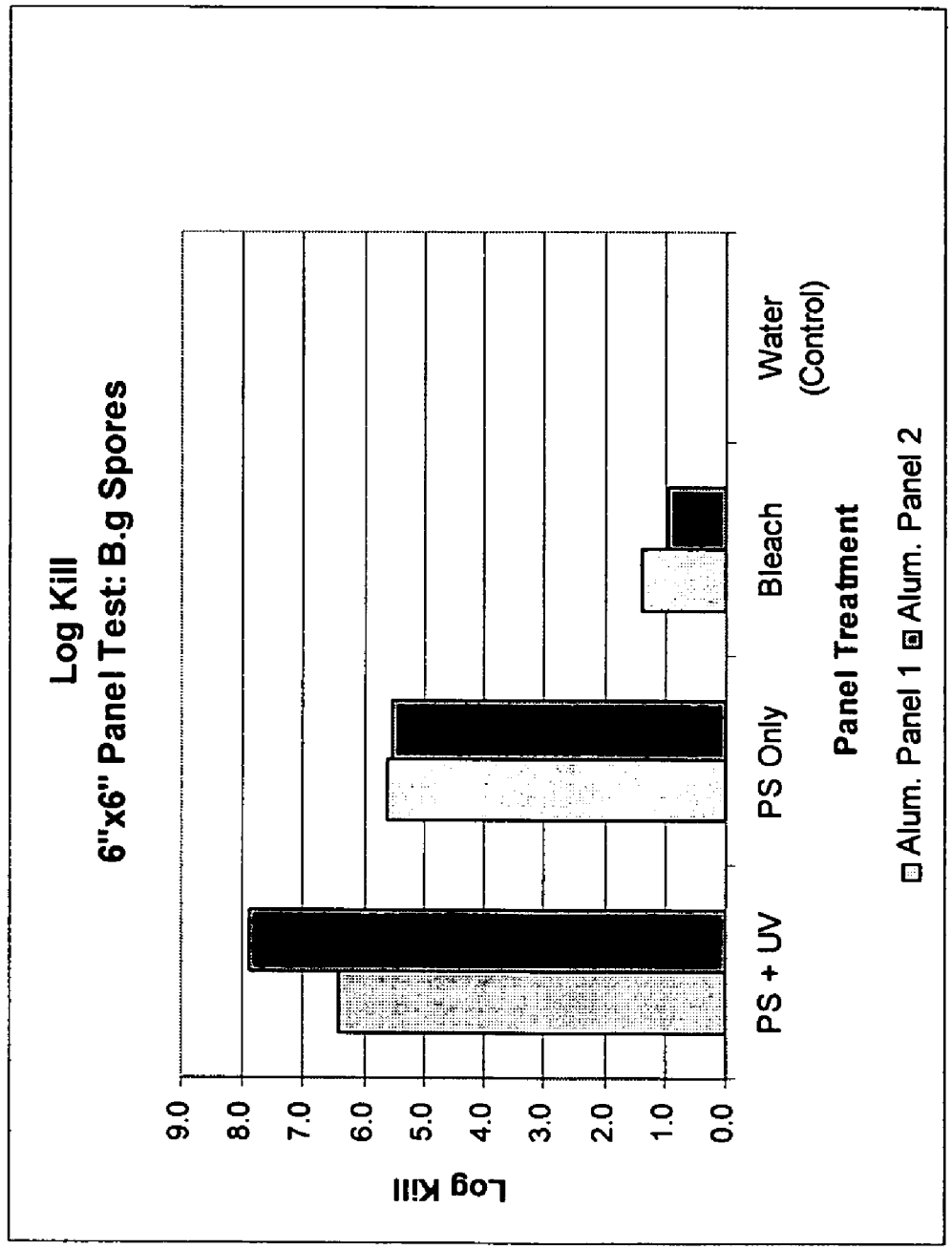

FIG. 13. Shown is the ME for killing dried Bg spores on 6 inch square panels. Compared are treatments by BDS ('PS Only'), BDS+high UV content light ('PS+UV'), bleach, and water (as a control).

Figure 14:
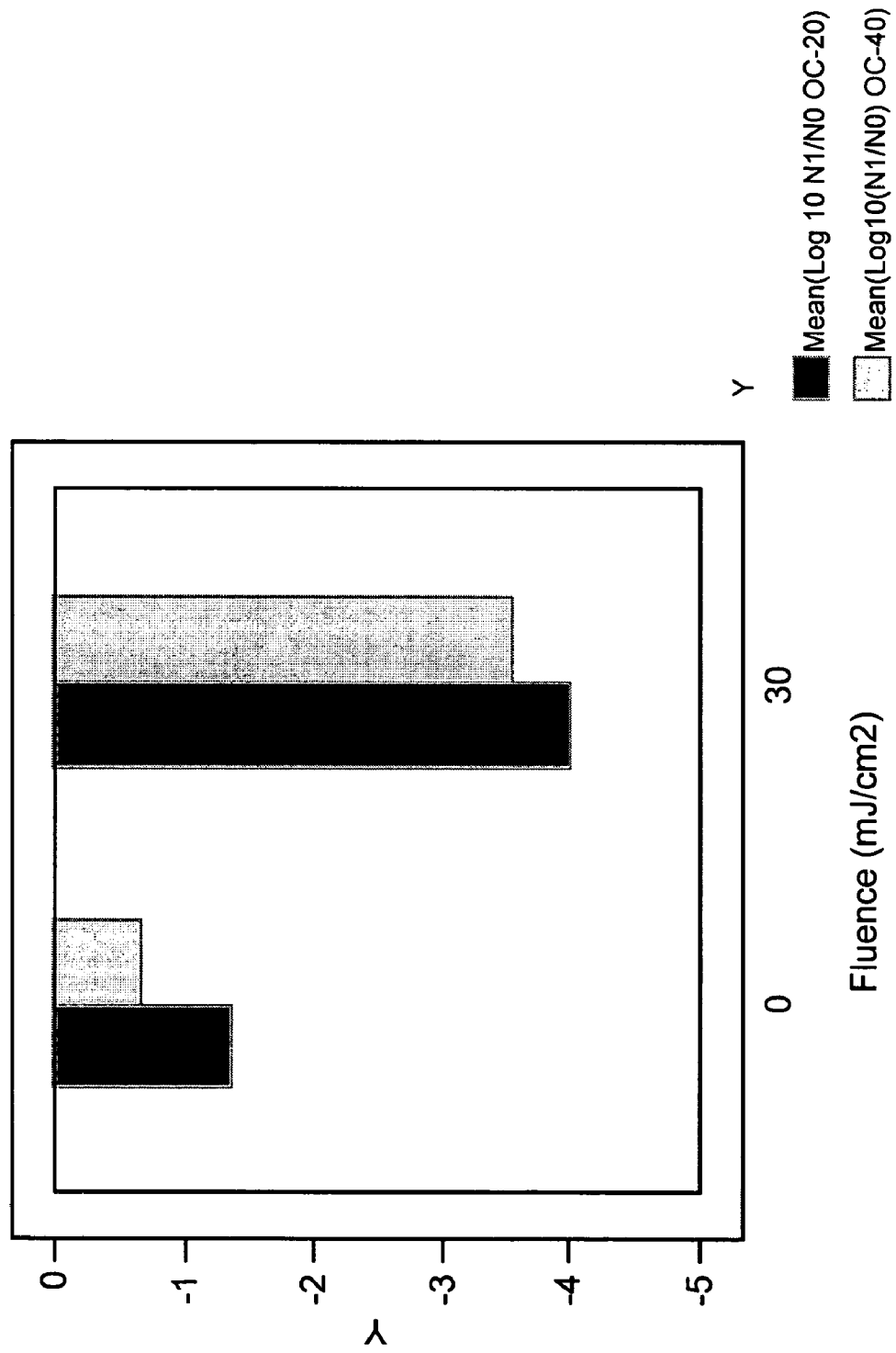

FIG. 14. Shown is a comparison of the ME for killing *E. coli* by BDS treatment (0 fluence) and BDS treatment with high UV content light (30 mJ/cm$^2$ fluence) for BDS formulated with two different phosphate ester surfactants, OC-20 and OC-40.

Figure 15:
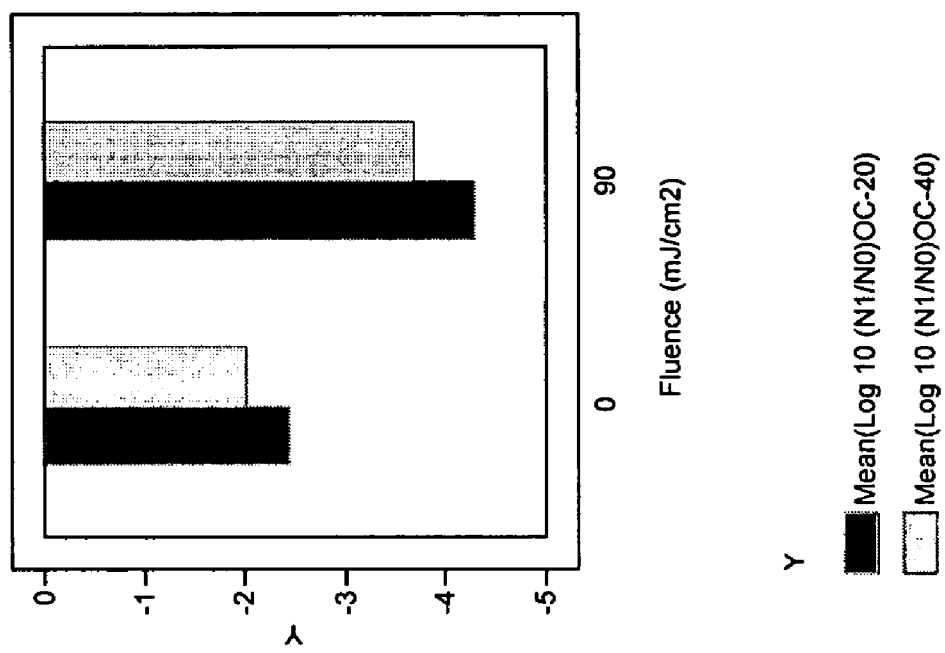

FIG. 15. Shown is a comparison of the ME for killing MS2 by BDS treatment (0 fluence) and BDS treatment with high UV content light (90 mJ/cm$^2$ fluence) for BDS formulated with two different phosphate ester surfactants, OC-20 and OC-40.

Figure 16:
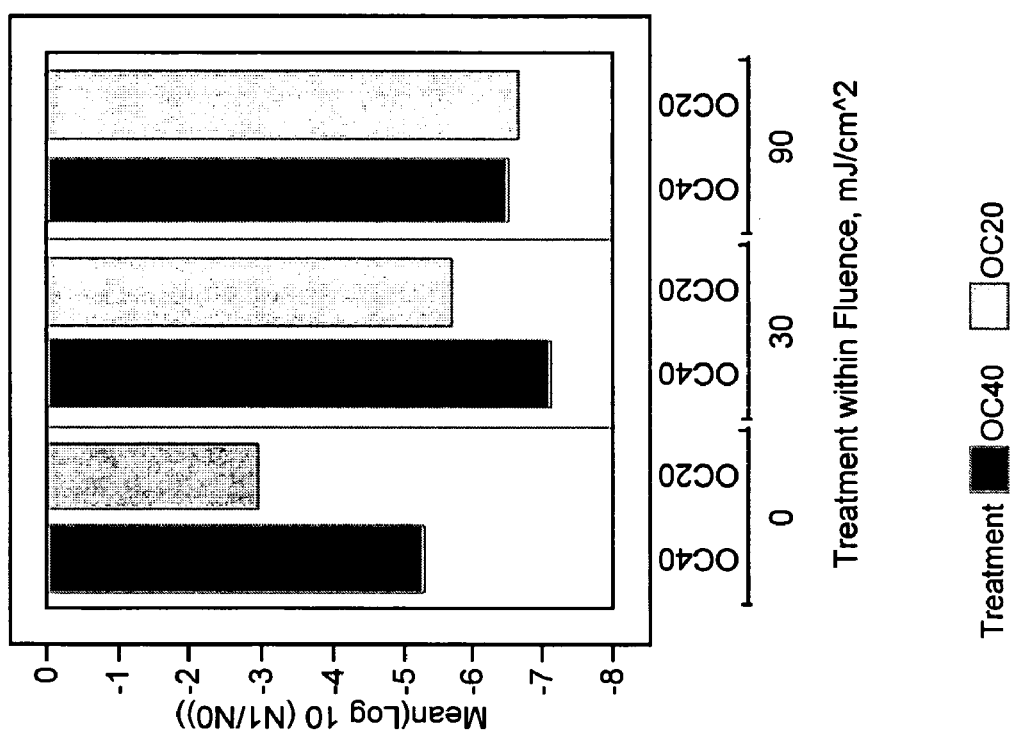

FIG. 16. Shown is a comparison of the ME for killing dried Bg spores by BDS treatment (0 fluence) and BDS treatment with high UV content light (30 mJ/cm$^2$ and 90 mJ/cm$^2$ fluences) for BDS formulated with two different phosphate ester surfactants, OC-20 and OC-40.

Figure 17:
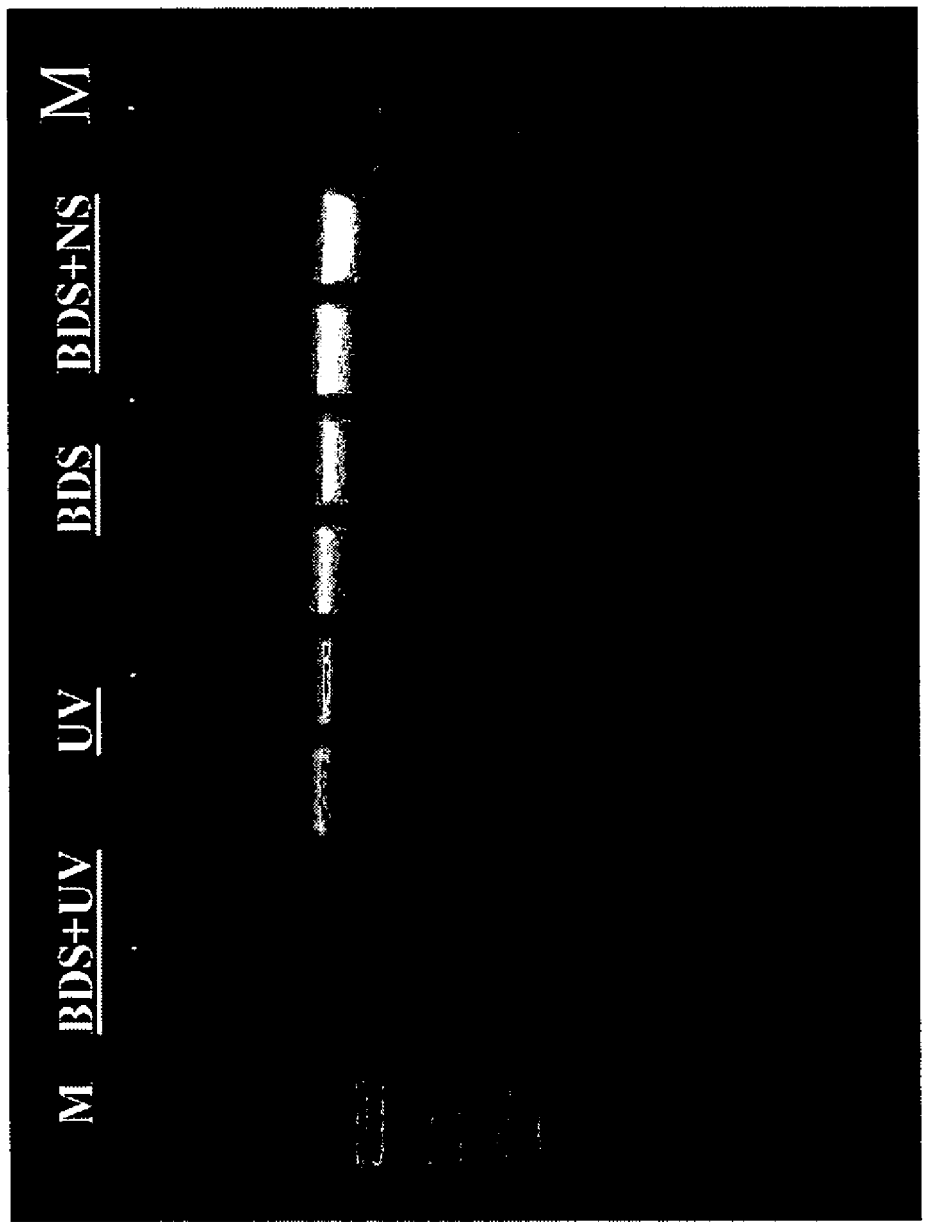

FIG. 17. T4 Endonuclease V Digestion of EDS Treated DNA shows the formation of T-T dimers.

Figure 18:
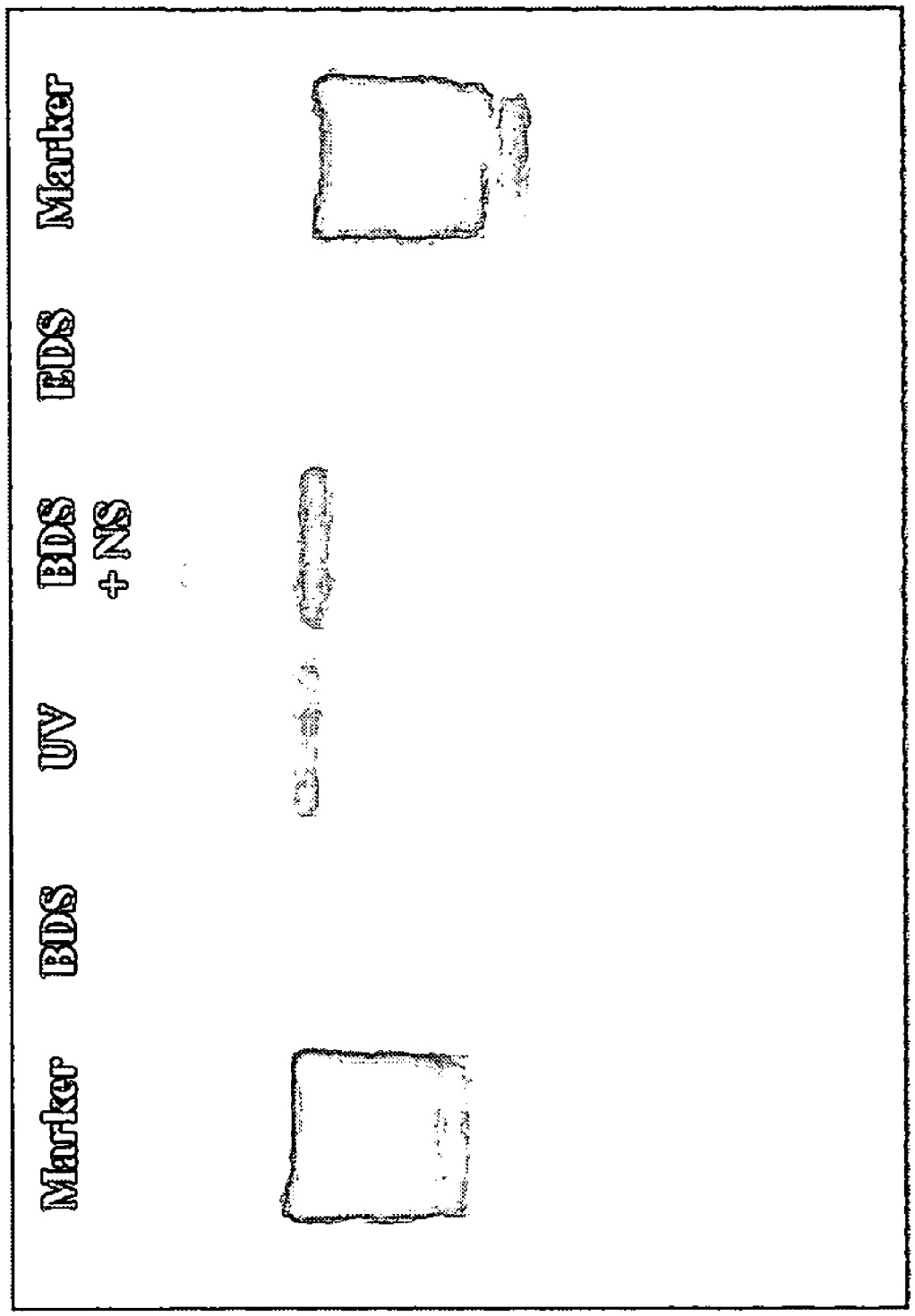

FIG. 18. EDS Destroys Spore DNA. Photosensitizer (PS) or UV alone result in insignificant destruction of DNA and neutralized PS (PS+N) shows no DNA destruction. However, EDS (PS+UV) shows significant destruction of DNA. M, molecular weight markers.

Figure 19:
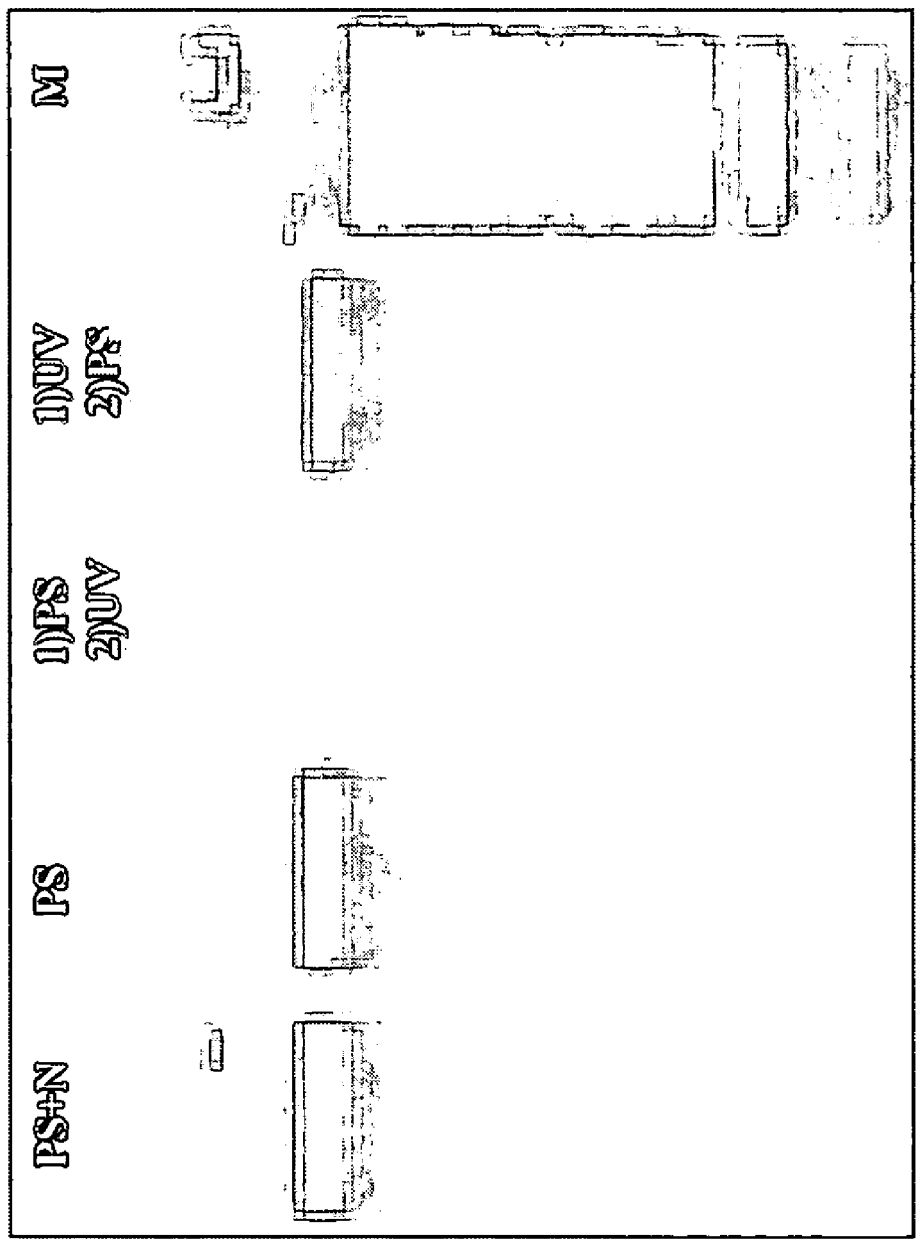

FIG. 19. The Synergistic Effect of BDS and UV Light. Four different treatments were applied to a challenge of $10^8$ spores. The samples were neutralized after the treatment and DNA was extracted with a MOBIO UltraClean™ Microbial DNA isolation kit.

Figure 20:
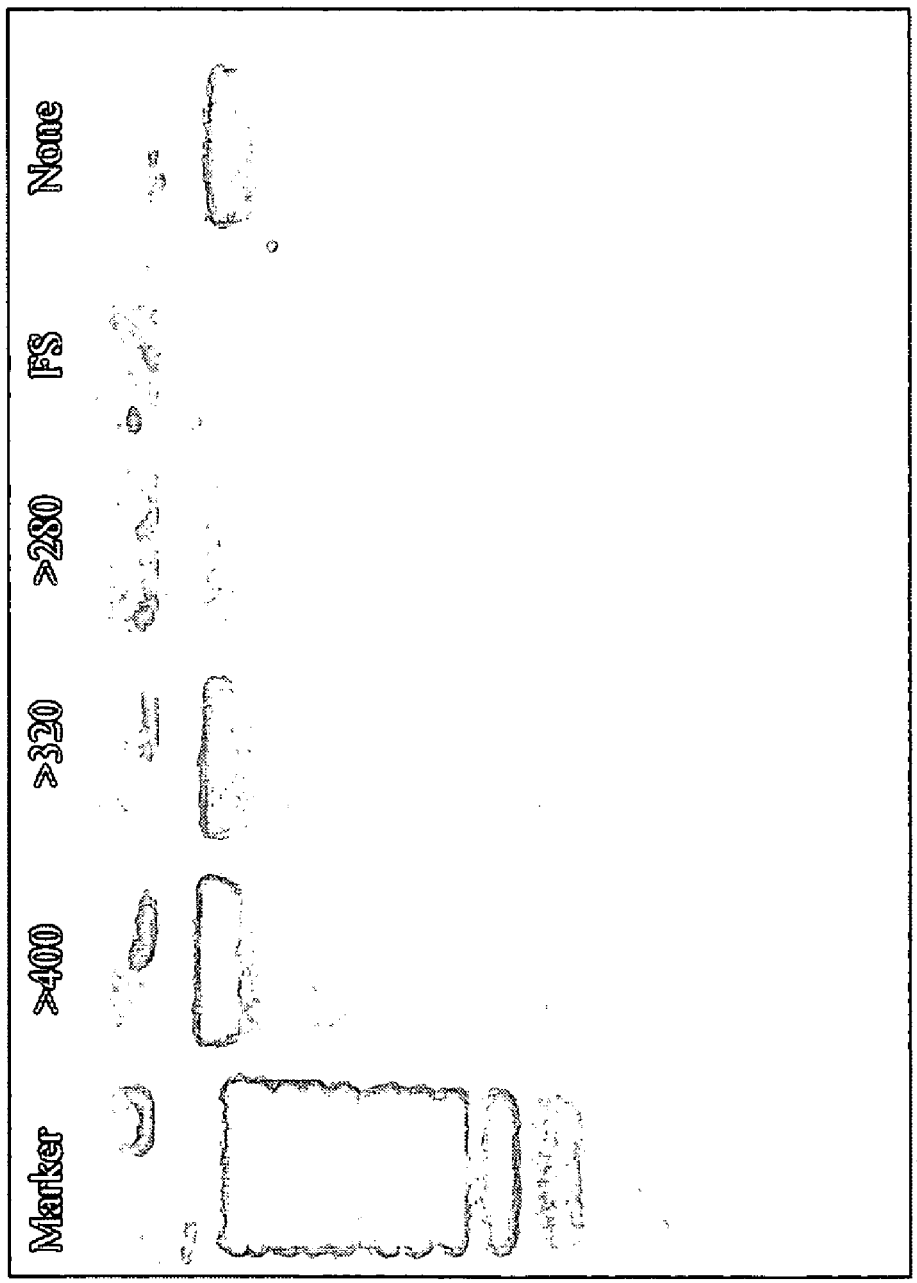

FIG. 20. The Effect of Various Wavelengths of Light on DNA Destruction.

Figure 21:
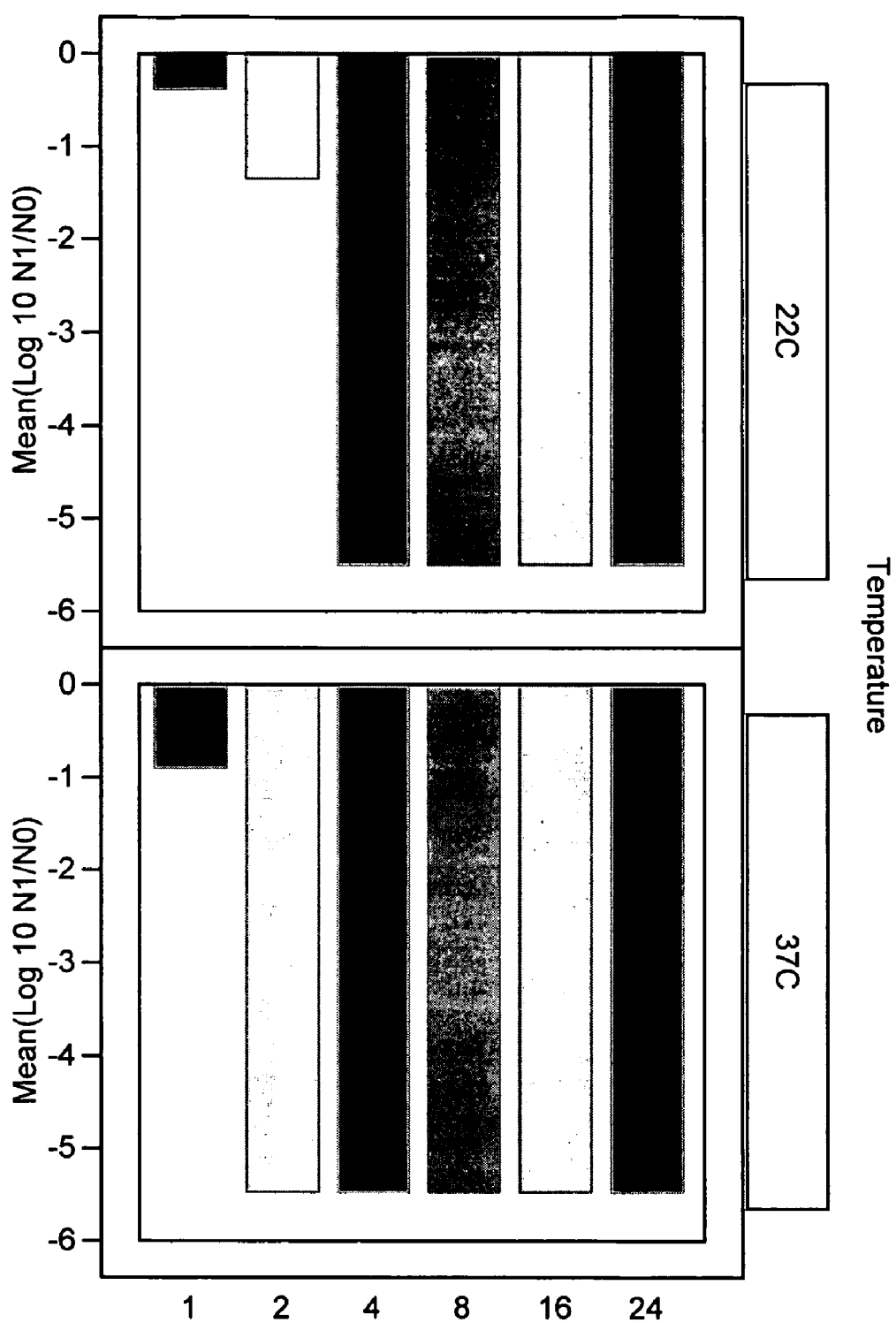

FIG. 21. The ME for killing Bg spores on test strips by BDS vapor.

Figure 22:
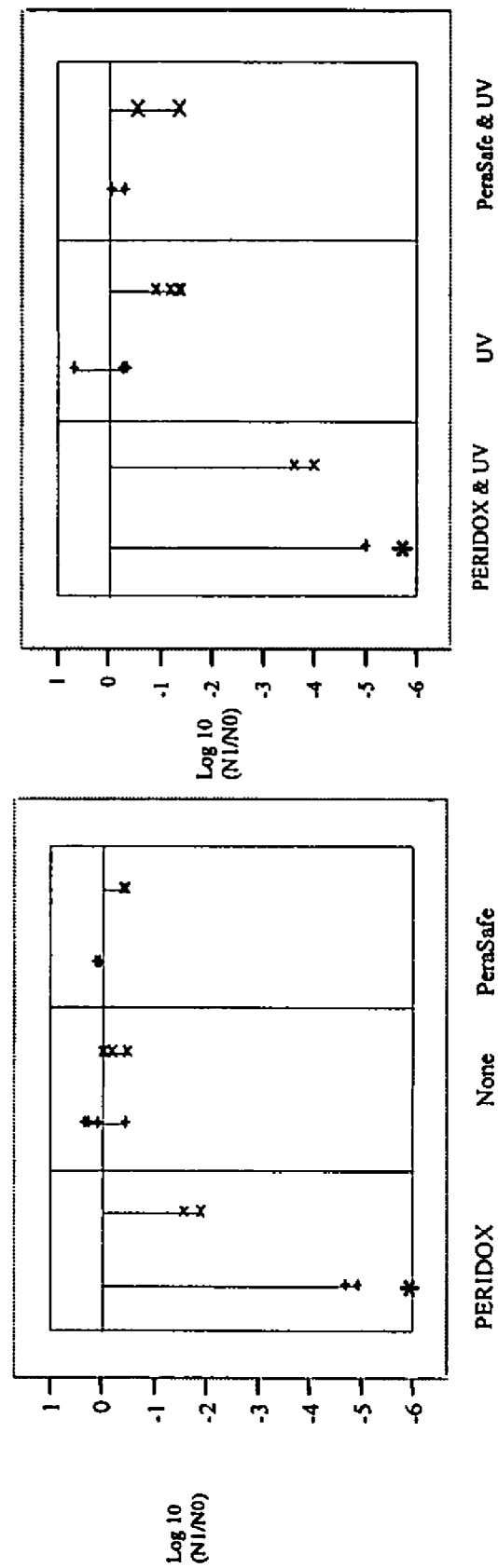

FIG. 22. Shown is a comparison of the ME of BDS (PERIDOX™) vs. PeraSafe™ (Antec International, Suffolk, England). For each of the various treatments, the bar on the left is the ME for killing Bg spores, and the bar on the right is the ME for killing MS2 bacteriophage. FIG. 22A: 'None' corresponds to a no-treatment control. FIG. 22B: 'UV' corresponds to treatment only by the high UV content light. Asterisk (*) indicates that no survivors were detected (data points represent the limit of detection for the trial). Data were acquired at CET.

Figure 23:
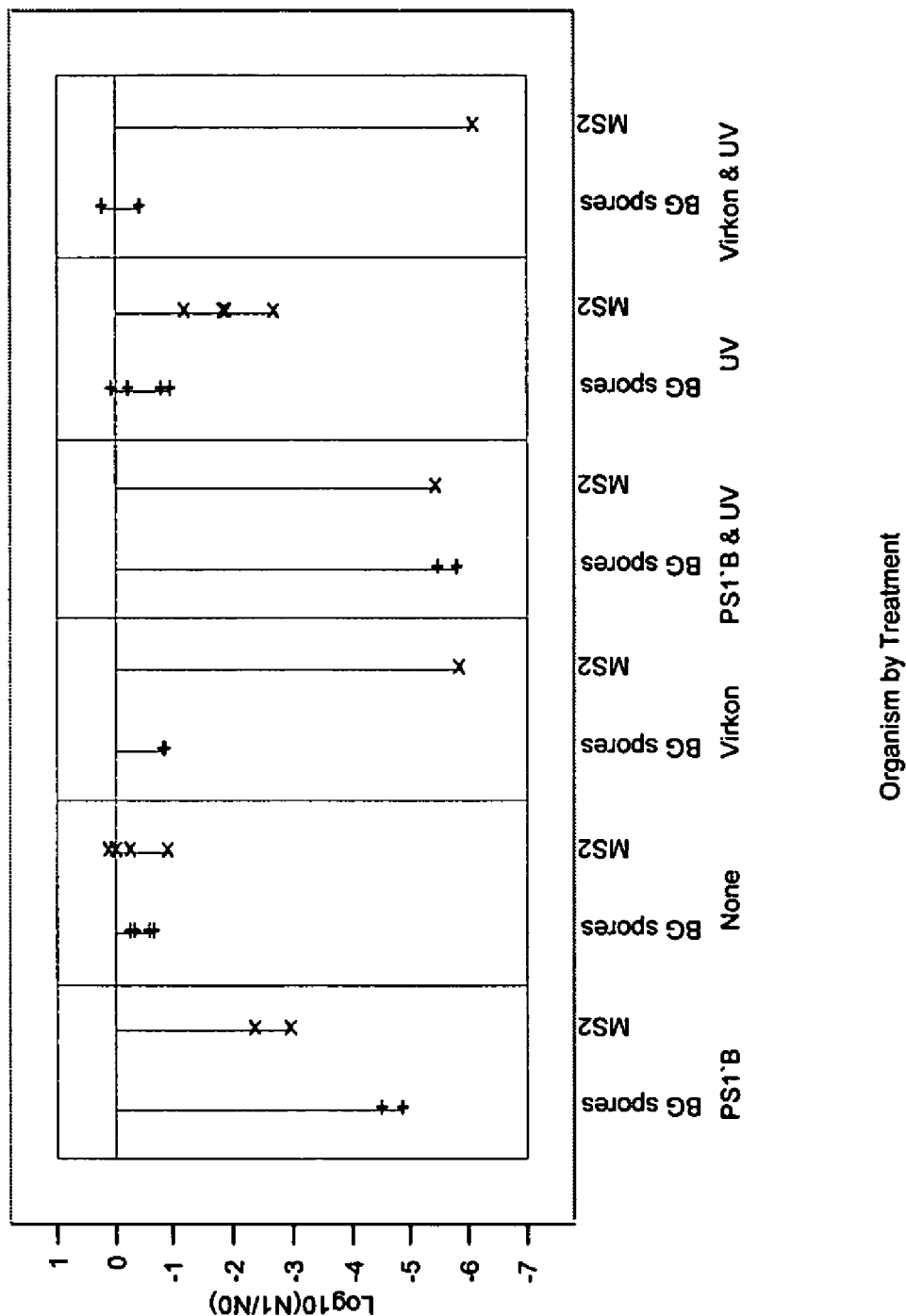

FIG. 23. Shown is a comparison of the ME of BDS ('PS1'B' in the figure) vs Virkon® (Biosafety USA, Sunrise, Fla.).

Figure 24:
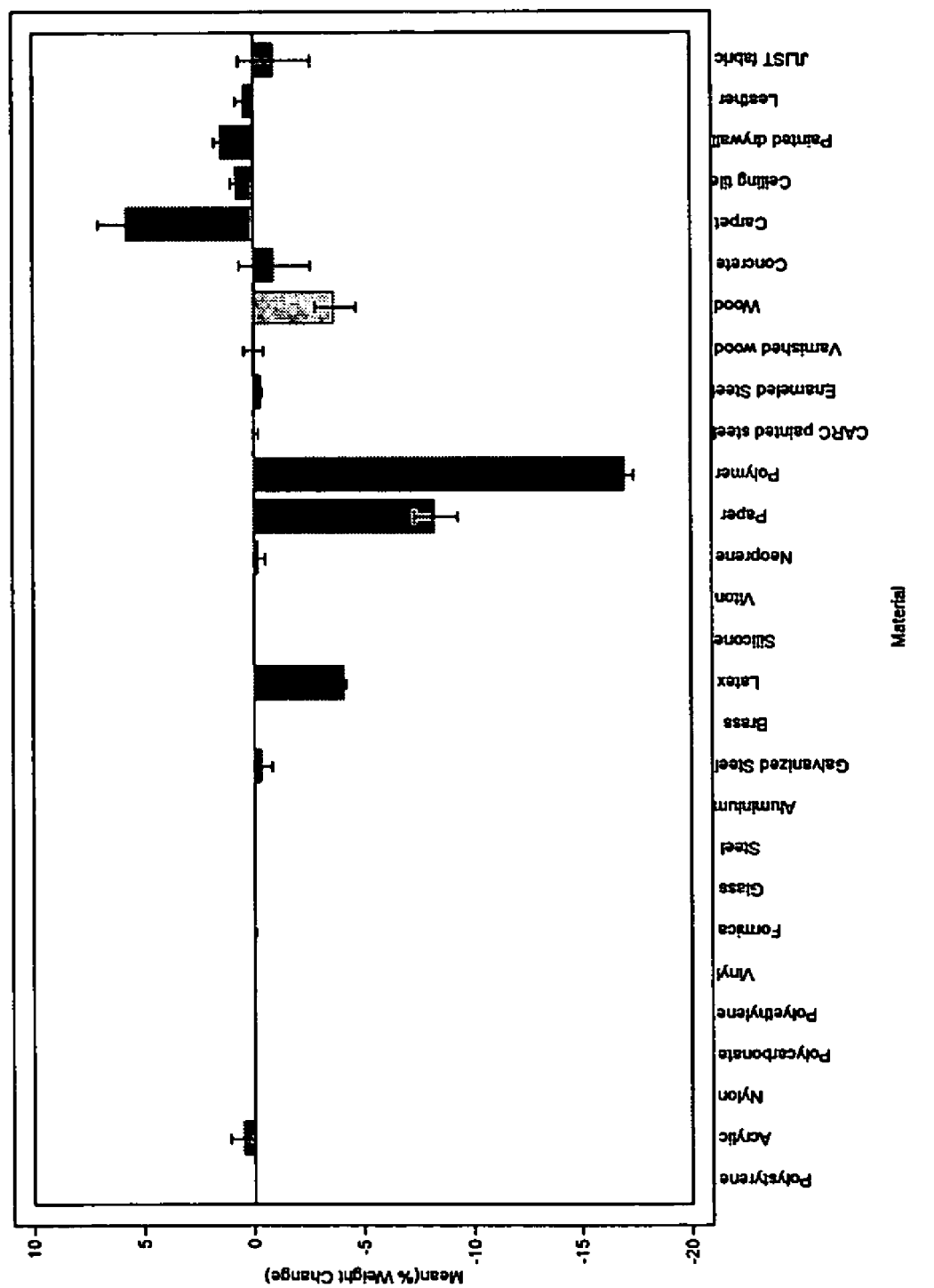

FIG. 24. Material Compatibility Test Results. The graph shows the mean % weight change of materials exposed to the BDS.

SUMMARY OF THE INVENTION

The invention is a microbicidal and fungicidal composition also capable of irreversibly destroying nucleic acids when used as a photosensitizer, containing: hydrogen peroxide or a peroxide precursor and activator; peroxyacetic acid; a water soluble polymer having one or more lactam groups, especially a polyvinyl polymer with a lactam; and a diester phosphorus surfactant having ethoxylates and attached alkyl or aromatic groups. In the composition, PVP is superior to methyl cellulose, PEG, and PPG because of its lactam group, which complexes with hydroperoxides, peroxides, and peracids. Also, PVP is known to more highly associate and form adducts with surfactants than other water-soluble polymers for adjusting rheological properties, such as viscosity building. Furthermore, the lactam-containing polymer and the photoreactive surfactant, each individually and also in combination, provide additional reactive chemistry that enhances the efficacy of the composition. The phosphorus ester surfactants further act also as stabilizers for the peroxide and the peracids, act to sequester metals, and improve wetting of the microbes to be killed by the composition, thereby aiding in bringing the microbicidal chemical species in proximity of the microbial target. The composition may also contain minor ingredients to enhance pharmaceutical elegance, such as odorants or dyes.

In one aspect the invention is a microbicidal and decontaminant composition comprising an aqueous solution of peroxides and peracids having equilibrium reaction products, a photoreactive surfactant, and a polymer, wherein the polymer interacts with the peroxides and the peracids.

In another aspect the invention is a sterilant composition comprising 4% hydrogen peroxide, 2000 ppm peroxyacetic acid, an equilibrium quantity of acetic acid, 0.1% to 1% polymer, and 0.05% to 0.5% phosphate ester surfactant.

In yet another aspect the invention is a binary microbicidal and decontaminant composition comprising a first part comprising a stabilized solution comprising hydrogen peroxide, acetic acid, and peroxyacetic acid; and a second part comprising a surfactant and a polymer, wherein the first part and the second part when mixed form a microbicidal solution.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

The composition of the present invention has outstanding ME with either or both dark action, i.e., unassisted by light, and with photochemical action, irreversibly destroys nucleic acids by photochemistry, and it also has low corrosivity, excellent Theological properties, and can be used sparingly and still result in thorough decontamination and disinfection. It is further the object of the present invention that in the dark mode it acts rapidly, e.g., accomplishes sterilization per the AOAC sterilant test with a contact time of not more than 45 minutes, and achieves greater than a six-log reduction (i.e., reduction by a factor of $10^{-6}$) in target microbial population as shown in the Surface Sterilization Test (SST) method (developed by Clean Earth Technologies, LLC) with a contact time of 3 minutes, and in the photochemical/photo-killing mode accomplishes sterilization within 1 minute. This rapid performance is very much better than prior compositions.

The anti-microbial composition of the present invention was developed in conjunction with the development of an Electrostatic Decontamination System (EDS), and the anti-microbial is will be available as a commercial product known as PERIDOX™. During its development, it has been also known as Biological Decontamination Solution (BDS) or denoted as photosensitizer, PS1'B. When used alone, i.e., without the subsequent application of light, PERIDOX™ is an effective anti-microbial that kills and inactivates. When PERIDOX™ is used as a photosensitizer with the subsequent application of light, the photo-sensitized killing is referred to as the 'EDS process'. When used without the subsequent application of light, the 'dark' microbicidal process is referred to as 'PERIDOX™ Only' or 'BDS Only'.

The composition is a microbicidal and fungicidal preparation also capable of irreversibly destroying nucleic acids when used as a photosensitizer, which comprises a peroxide and peracid aqueous solution with the addition of a hydrophilic polymer and an anionic phosphate surfactant. The polymer and surfactant are selected to have a high association with each other, i.e., a high adsorption, and also to readily complex with the peroxide or peracid and the reactive, microbicidal species. Further, the polymer and surfactant are selected for several additional properties, which include wetting of surfaces (both microbial and substrate), corrosion inhibition, metals sequestering, and also assisting in photochemical reactions that contribute to microbicidal efficacy. When used in efficacious concentration, the polymer and surfactant do not sufficiently compete as light absorbers so as to adversely affect microbicidal efficacy.

The formulations of the composition exploit the unique interaction of hydrophilic and amphiphilic polymers, especially nonionic polymers, which include, but are not limited to, PVP (polyvinyl pyrrolidone) and PVA (polyvinyl alcohol) with anionic phosphate surfactants. Examples are mono-ester and diester phosphates, of which OC-20 and OC-40 (manufactured by Dexter Chemicals of N.Y.) are efficacious examples. In one embodiment, the surfactant has an R-terminal lipophilic alkyl hydrocarbon chain in a range of C9 thru C13, a hydrophilic PEO polyoxyethylene chain in a range of PEO-3 to PEO-9 and a Z-terminal mono- and diester-phosphate. In another embodiment, an aromatic compound, for example a nonyl phenol, is the R-terminal group instead of the alkyl chain of the previous example.

The polymer-surfactant interaction provides for effective wetting and dispersion in the pH range that is required for the equilibrium stability of hydrogen peroxide. The unique aqueous soluble polymer-surfactant interaction provides a filin-forming capability to the formulation. Such a film-forming capability is required for anti-corrosive effectiveness on metal surfaces and stabilization of rheological and dielectric properties of the formulations when utilized in electrostatic spray applications. The adjusted rheological properties must balance sprayability (low viscosity) and good film-forming (sufficient viscosity and adhesion), which is necessary to avoid excessive run-off of the formulation when sprayed onto a surface.

The composition may be prepared and stored for long periods, for example for more than one year, as a complete concentrate and longer when stored in two parts. The binary solutions comprise, in one part, a stabilized peroxide and peracid solution and, in the second part, a solution of polymer and surfactant. It is understood that either part may also contain minors comprising odorants, fragrance, dyes, sequestrants, stabilizers, or other ingredients that give improved storage characteristics to the binary parts or pharmaceutical elegance to the combined solutions, but these minors must be selected to not absorb light sufficiently or scavenge microbicidal chemical species to the extent that the microbicidal efficacy of the composition is unacceptably degraded. The concentrated peroxide/peracid solution may have a peroxide concentration from 2 to 50% by weight. A concentration of hydrogen peroxide in the range of 24 to 28% is preferred. The concentration of the peracid, especially peroxyacetic acid (PAA), is in the range of 1% to 50% of the hydrogen peroxide concentration by weight. The preferred PAA concentration is in the range of 4% to 8% of the hydrogen peroxide concentration. The polymer and surfactant solution may be a concentrate in a ratio, which is in the range of 1:1 to 20:1 by weight and dissolved in sufficient water to permit ready pouring and mixing with the peroxide/peracid solution, and then after such mixing, a balance of water is added so that the polymer fraction of the solution is in the range of 0.1% to 3%. In another embodiment, the polymer/surfactant may be dissolved in sufficient water so that upon mixing with the peroxide/peracid solution, no additional water is needed to obtain the desired fractions of polymer and surfactant in the mixture.

The formulation of the concentrated microbicidal composition, which is called concentrated 'Biological Decontamination Solution', concentrated 'BDS', concentrated photosensitizer "PS1'B", or 'PERIDOX™' concentrate, is shown in Table I below.

TABLE I

Formulation of BDS Concentrate

| Formula | Material | Quantity | |
|---|---|---|---|
| 24% $H_2O_2$ | $H_2O_2$ 30% | 3.025 | L/Gal |
| 1.2% PAA | PAA 32% | 0.014 | L/Gal |
| 0.6% PVP | PVP (10K) | 0.0227 | Kg/Gal |
| 0.6% OC-40 | OC-40 | 0.0227 | Kg/Gal |
| Balance | Water | | |

The composition may also be prepared as a ready-to-use solution. A preferred formulation for use as a sterilant or as a sprayed photosensitizer and comprising 4% hydrogen peroxide, 0.2% PAA, 0.1% polymer, and 0.1% surfactant has been extensively tested. A lower concentration solution may be used for germicidal or sanitizer applications. Various tests have been performed to support the registration of the composition (with the trade name PERIDOX™) with the US EPA in accordance with the Federal Insecticide, Fungicide, Rodenticide Act (FIFRA). Table II lists the tests, the test organisms, and the number of tests passed in support of the product registration. As part of the FIFRA registration process, the US EPA has reviewed the product master label, which states recommended uses, use concentrations of the composition and contact times, and directions for use. Also shown in the table are the recommended contact time and concentration. The AOAC Germicidal Spray & Use Dilution tests for the 7 organisms shown in Table II were successfully passed with 5 minute contact time and 2% concentration. However, consistent with US EPA guidelines, a single contact time and concentration were recommended on the label for product use as a disinfectant. Test results for various organisms are given in Tables III. Testing in support of product registration was performed at Microbiotest, Inc. (Sterling, Va.) and ATS Laboratories (Eagan, Minn.). Testing with pathogens and confirmatory testing was also performed at the Battelle Memorial Institutes' Columbus Operations (BCO, Columbus, Ohio) and at the Midwest Research Institute (MRI, Kansas City, Mo.). Testing was performed with PERIDOX™ concentrate diluted with hard water (250 ppm $CaCO_3$).

An example of the dilute composition comprises a solution of 4% hydrogen peroxide, 2000 ppm of peracetic acid, 0.1% of OC-20 or OC-40 surfactant, and 0.1% of PVP along with an equilibrium quantity of acetic acid and a balance of makeup water. This composition is denoted as Biological Decontamination Solution or 'BDS', also as 'PS1'B', and also as 'PERIDOX™' in the test results given in the following examples. The strength of the photosensitizer is referred to by the concentration of hydrogen peroxide in the composition. Thus, a 4% photosensitizer contains 4% hydrogen peroxide.

Good microbicidal efficacy can be obtained with variations in the BDS formulation as a dilute solution. These variations include hydrogen peroxide in the concentration range of 0.1 to 10%, where concentrations below 6% are more conducive to BDS use as a photosensitizer, PAA concentration in the range of 50 ppm to 1%, higher being more effective in countering the effects of high protein or enzyme challenge, lower having lower corrosivity, and polymer concentration in the range 0.015 to 2%, a concentration of about 0.1 to 0.2% being an effective balance of rheological properties and efficacy properties.

TABLE II

Tests that BDS has Passed for FIFRA Registration and Recommended Contact Time and Concentration

| Test | Organism | N | Contact Time (minutes) | Concentration (%) |
|---|---|---|---|---|
| AOAC Germicidal & Detergent Sanitizing Action of Disinfectants/ Fungicidal Spray | Staphylococcus aureus | 6 | 1 | 2 |
| | Escherichia coli | 6 | 1 | 2 |
| | Candida albicans | 20 | 10 | 4 |
| | Trichophyton mentagrophytes | 20 | 10 | 4 |
| AOAC Sporicidal Activity | Bacillus subtilis | 720 | 45 | 4 |
| | Clostridium sporogenes | 720 | 45 | 4 |
| AOAC Germicidal Spray & Use Dilution | Staphylococcus aureus | 60 | 10 | 4 |
| | Pseudomonas aeruginosa | 60 | 10 | 4 |
| | Salmonella choleraesuis | 60 | 10 | 4 |
| | Listeria monocytogenes | 20 | 10 | 4 |
| | Enterobacter aerogenes | 20 | 10 | 4 |
| | Vibrio cholerae | 20 | 10 | 4 |
| | Salmonella typhimurium | 20 | 10 | 4 |
| Tuberculocidal | Mycobacterium bovis | 20 | 10 | 4 |

TABLE II-continued

Tests that BDS has Passed for FIFRA Registration and Recommended Contact Time and Concentration

| Test | Organism | N | Contact Time (minutes) | Concentration (%) |
|---|---|---|---|---|
| Virucidal efficacy | Avian Influenza A (H3N2) | 2 | 10 | 4 |
| | Reovirus | 2 | 10 | 4 |
| | Human Coronavirus | 2 | 10 | 4 |

TABLE III

Test results Showing Contact Time and Efficacy of BDS against Pathogenic Viruses

| VIRUS | N | CONTACT TIME (min) | LOG KILL |
|---|---|---|---|
| Poliovirus Type 1 | 3 | 30 | 4.5* |
| Influenza B/Lee | 3 | 10 | 5.8* |
| Influenza A/Hong Kong | 3 | 10 | 6.0* |
| Avian Influenza A | 2 | 10 | 5.25* |
| Human Coronavirus | 2 | 10 | 3.0* |
| Reovirus | 2 | 10 | 5.75* |
| Hepatitis A | 2 | 30 | 7.0* |

Testing was performed at Microbiotest (Sterling, VA) and ATS Labs (Eagan, MN).

The composition may be used either with or without light activation and photo-killing. Without the light, the composition may be used for killing microbes (e.g., bacteria, spores, and/or viruses) or fungi in aqueous liquids, on surfaces, or in the air. The microbicide may be applied as a liquid or sprayed as an aerosol. Methods of application include, but are not limited to, spraying, pouring, brushing, wiping with wetted wipes, sponging, mopping, evaporating, and other means. The composition may be applied to hard, non-porous, or porous surfaces. Objects may be dipped or immersed in the composition or exposed to it as vapor or aerosol. Microbicidal efficacy results with adequate contact time and concentration.

As a photosensitizer with light activation, the composition is applied and then, after an interval that exceeds a specified contact time, the object, surface, or volume of air is illuminated with light. The application of intense light that has a significant content of ultraviolet light of wavelength in the range 170 nm to 400 nm, and especially in the spectral wavelength region of 210 nm to 310 nm, onto the photosensitizer will result in irreversible destruction of the nucleic acid compounds in the microbes in addition to other killing mechanisms. It is also found that spore killing can be accomplished with the light pulses from an intense Xenon flashlamp for which the UV content of the light spectrum is removed by filters.

For efficient transfer, the composition may be applied by electrostatic spraying. An example of electrostatic spraying is described in U.S. Pat. No. 6,692,694 B1. Electrostatic spraying may be used for dissemination onto accessible surfaces, for application onto non-line-of-sight surfaces, and also for enhancing the interaction with aerosol contamination and within aerosol clouds.

When applied onto a relatively non-porous surface (a so-called 'hard' surface), a typical application rate is 25 to 100 ml/m². This corresponds to a film thickness of 25 to 100 μm. Much thicker films are not as conducive to photo-activation and photo-killing because of absorption of photons in the photosensitizer occurs in locations in the liquid layer that are too distant from the target microbes for the microbicidal photo-reaction products to reach them. However, much thicker films may be more effective for dark reaction microbicidal efficacy because the additional active ingredients can provide a better stoichiometric advantage when there is a substantial amount of protein or enzyme load on the surface, e.g., serum or catalase. A typical contact time of one minute and subsequent exposure to light from an intense, pulsed xenon flashlamp and amounting to at least 45 mJ/cm$^2$ of UV light is sufficient to kill microbes and irreversibly destroy nucleic acids on a 'hard' surface to the level of detection, i.e., the number of colony forming units (CFU) or plaque forming units (PFU) after sampling/recovery, plating, incubation, and enumeration are below a statistically meaningful level. Although a fluence of 45 mJ/cm$^2$ of UV light is sufficient to kill microbes in many circumstances, the exact fluence may be higher or lower depending a number of factors such as the contact time prior to UV illumination, ambient temperature, and organic load on the surface, and in one embodiment the fluence ranges from 15-90 mJ/cm$^2$.

Immersion killing without regrowth is obtained with contact times that are less than one hour at room temperature. Immersion tests with penicylinders inoculated with *Bacillus subtilis* or *Clostridium sporogenes* and subjected to a 9 minute contact time with the microbicidal composition showed no regrowth. Similarly-inoculated silk suture loops subjected to a 45 minute contact time showed no regrowth.

As an aerosol spray, it is found that a concentration on the order of 0.1 to 1 g/m$^3$ is sufficient to obtain thorough kill in a volume of air at room temperature with a contact time in the range of 5 to 15 minutes. Such a concentration of aerosol also provides liquid and vapor killing on the surfaces enclosing the volume.

The microbicidal composition has been tested on a variety of 'hard' and porous surfaces. It is found that excellent microbicidal efficacy is obtained without adversely affecting materials. The intended use for the composition is by healthcare providers, workers in veterinary care, food preparation and production, in the pharmaceutical and electronics industries, and by the United States military, civil support teams, and local emergency response teams. Anticipated uses are sanitation and disinfection to promote the reduction in the occurrence of nosocomial infections and horizontal transfer of drug resistance among bacteria in hospitals and other health care facilities, and in ambulances, and the spread of communicable diseases in transportation systems (airplanes, ships, etc.) rapidly and with little interruption in operations.

Initial product registration of PERIDOX™ per FIFRA was approved on Oct. 20, 2005 as US EPA Registration Number 81073-1. Approved uses include: biological decontamination of hard and nonporous surfaces, biological disinfection of hard and nonporous surfaces, sanitizing rinse on previously cleaned nonporous food contact surfaces, Sterilant for Aseptic Manufacturing and Packaging Equipment, Disinfectant for the Pharmaceutical and Cosmetic Industry, Sterilant/Disinfectant for Non-patient Contact for Healthcare and Veterinary Facilities, Delivers antimicrobial activity on yeast, molds and bacteria. Product claims include "Effective against a wide range of viruses, bacteria and fungi, including" the organisms listed in Table II. It is a disinfectant for "Hospitals, Nursing Homes, Health Care Facilities, Schools, Colleges, Veterinary Clinics, Animal Life Science Laboratories, Industrial Facilities, Dietary Areas, Office Buildings, Recreational Facilities, Retail and Wholesale Establishments, Animal Care Facilities, Veterinary Facilities, Farms, Livestock Quarters, Poultry Premises, Poultry Hatcheries, and vehicles including ships, planes, automobiles, trucks, trains, and EMS" (emergency medical systems). Registered uses include: disinfection (combination disinfection and cleaning, virucidal, fungicidal, tuberculoidal, and disinfection of pharmaceutical and cosmetic surfaces), antimicrobial treatment (sterilization of manufacturing, filling and packaging equipment in aseptic processes, sterilian for non-patient contact surfaces for healthcare and veterinary facilities), and sanitization (sanitization rinse on pre-cleaned non-porous food contact surfaces).

Testing

Extensive testing of the microbicidal efficacy and other performance tests of the microbicidal composition has been done as part of the development of an Electrostatic Decontamination System (EDS). The EDS accomplishes disinfection or decontamination treatment of a surface or aerosol by spray application of the composition and its subsequent illumination by pulsed light. Because the light cannot reach non-line-of-sight places, and it does not penetrate deeply into porous or textured materials, the successful treatment also relies on the disinfecting and decontaminating properties of the composition in the absence of light. Thus, the testing has been performed to demonstrate both dark killing and photoactivated killing.

In the tests, the microbicidal efficacy (ME) and the decontamination effectiveness (DE) are determined under various conditions and with various formulations of the composition as a photosensitizer/disinfectant/sterilant/or decontaminant. In addition, standard tests, e.g., AOAC sporicidal tests, virucidal, bactericidal, fungicidal efficacy tests, and use dilution tests have been performed as part of the demonstration of efficacy and directions for use, which are required for regulatory registration and approval of the composition. Further tests also include the measurement of ME as a function of process parameters. These parameters include the pulsed light parameters such as light intensity, number of pulses, pulse rate, distance between the light source and test surfaces, and others.

Among the various tests are those to determine the ME for the photosensitized ultraviolet disinfection of dried Bg spores, dried MS2 bacteriophage virus, and vegetative *E. coli* bacteria. Tests are performed by inoculating a test surface with the subject organism, drying the inoculum, spraying or pipetting the photosensitizer/disinfectant onto the inoculated surface, and, after one minute of contact, illuminating the surface, microbes, and photosensitizer with light from CET's intense pulsed flashlamp UV light source. The initial challenge inoculum is titered to determine its concentration. After the treatment, the photosensitizer is neutralized and its disinfection action stopped by the addition of neutralizing solution. The population of surviving microbes is determined by subsequent serial dilutions, plating, incubation and enumeration. The tests are repeated with varied exposure times to obtain treatment with various fluences. In this manner, 'kill curves' are determined.

Comparative tests have been made with previous photosensitizer compositions such as Zerotol™, which is a commercial soil drench, hydrogen peroxide, and compositions comprising aqueous solutions made of hydrogen peroxide and peracetic acid, and various ingredients selected from the following: acetic acid, anionic surfactant, and polymer. A typical composition having all of these ingredients except polymer is denoted as 'PS1 photosensitizer' in the examples described below.

Tests have also been performed to determine the material compatibility of the new photosensitizer composition by investigating its anti-corrosive properties. The tests comprise 48 hour immersion in BDS of selected materials such as plastics, rubbers, metal, and other common materials as test coupons. Weight change, corrosion, solution pH change, and hardness are measured. It is found that the composition exhibits superior anti-corrosion properties in contrast to other compositions containing peroxy/peracid mixtures.

Furthermore, tests have also been performed to investigate the sprayability, surface wetting properties, and coating properties of the new composition. It is found that the new composition also has excellent surface wetting properties, is amenable to electrostatic and non-electrostatic spraying, and can be applied with very high transfer efficiency to thoroughly coat the target surface to be disinfected/decontaminated. In conjunction with these tests, the physical properties, e.g., the surface tension, viscosity, and photo-oxidative potential of the BDS have been determined, and comparison with other compositions have been made.

Materials & Methods

Strains and Growth Conditions

Tests include a variety of biological surrogates and pathogens. The BDS solution was tested against Gram-positive and Gram-negative bacterial vegetative cells (*Bacillus atrophaeus, Staphylococcus aureus*, and *Escherichia coli*), *Bacillus* spores (*B. atrophaeus* and *B. anthracis*), and bacteriophage MS2 at high challenge levels. Surrogate testing is necessary for process development, solution development, and test method and procedure development because of issues of affordability, safety, and cost.

Choices for biological surrogates (Table IV) were made for good fidelity with test results for pathogens. *Bacillus atrophaeus* (also called *Bacillus globigii*, or Bg) spores were the surrogate for *Bacillus anthracis* (Ba) spores. Bg has traditionally been used by researchers for this purpose. Likewise, the virus MS2 is commonly used as a surrogate for viral pathogens because it is difficult to destroy and it is easy to assay. For bacterial surrogates, common laboratory strains of *E. coli* and *B. atrophaeus* were chosen to represent the Gram negative and Gram positive pathogens, respectively. For the pathogen *S. aureus*, no surrogate was chosen. Instead, the agent was used directly.

TABLE IV

Biological Challenges

| TYPE | SURROGATE | PATHOGEN |
|---|---|---|
| Spore | B. atrophaeus | B. anthracis |
| Gram positive vegetative cell | B. atrophaeus | S. aureus |
| Gram negative vegetative cell | E. coli | None |
| Virus | MS2 (Host: E. coli) | None |

All Bg and Ba spores were obtained from BCO. Bg (Pine Bluff strain) was validated by gas chromatography-fatty acid methyl ester (GC-FAME) analysis at Midi Laboratories (Newark, Del.). Bg spores were grown in fermentor batches in modified G medium (yeast extract, 2.0 g/L; $(NH_4)_2SO_4$, 2.0 g/l, $CaCl_2.2H_2O$, 25 mg/l; $CuSO_4.5H_2O$, 5.0 mg/l; $FeSO_4.7H_2O$, 0.5 mg/l; $MgSO_4.7H_2O$, 0.2 g/l, $MnSO_4.4H_2O$, 50 mg/l; $ZnSO_4.7H_2O$, 5.0 mg/l) at 30° C. Ba (Ames) was validated by DNA fingerprinting and protective antigen (PA) gene sequencing. Spores were grown in fermentor batches in Leighton-Doi medium (nutrient broth, 16 g/l; KCl, 1.88 g/l; $CaCl_2$, 0.294 g/l; $FeSO_4.7H_2O$, 2.7 mg/l; $MnSO_4.7H_2O$, 1.7 mg/l; $MgSO_4.7H_2O$, 24.6 mg/l; dextrose, 0.9 g/l) at 37° C.

*Escherichia coli* (ATCC 15597, and its bacteriophage MS2 [ATCC 15597 B1]) were originally obtained from American Type Culture Collection (ATCC, Manassas, Va.). The dried viral stock was resuspended according to the accompanying instructions and filtered using a Whatman Puradisc™ 25AS 0.2 µm syringe filter. The titer of this stock was determined to be $5 \times 10^8$ PFU/ml. The phage stock was stored at 4° C. The bacterial stock was maintained on a nutrient agar slant, which was re-streaked once per month. Isolated colonies were obtained by streaking the slant stock on Luria Broth (LB)-agar plates. Overnight cultures were grown from isolated colonies picked from plates at CET and BCO in 5 ml LB at 37° C. as needed. The *E. coli* strain was validated periodically by confirming the MS2 phage sensitivity on LB-agar medium. All prepared media was purchased from Remel (Lenexa, Kans.) or Biomerieux (Lombard, Ill.).

*S. aureus* [ATCC 14458 (SEB enterotoxin)] were grown at BCO in 25 ml Tryptic Soy Broth (TSB) in a 125 ml flask at 35-37° C. at 200 rpm for ~16 hours. The cultures generally grew to $3 \times 10^9$ CFU/ml.

Biological Decon Solution (BDS)

The embodiment of the microbicidal composition, BDS was typically prepared as a concentrate and is diluted at the time of the experiment. The percent concentration refers to the final concentration of the hydrogen peroxide. Thus, in a preferred embodiment, the concentrate is 24% and the working solutions range from 0.1% to 4%. For laboratory experiments, ultra pure water is used for dilution. However, ME has been tested when the water source came from the city water supply, ocean, or river, and no difference in efficacy has been observed.

UV Light Source

The fluence (time-integrated, incident UV light energy per unit area for photons in the spectral range of 210-310 nm) is determined by time integration of the local measurement (active area <1 $mm^2$) of the light flux as measured with a set of SiC solar-blind photodiodes that are positioned at a known distance from the xenon flashlamp. Prior to each test, the flashlamp is calibrated by measuring and recording the output of 64 pulses of light. The values are averaged and this number is used to determine the length of time (or number of pulses) required for the desired fluence. The fluence is calibrated against a traceable light standard lamp with the use of the measured spectral intensity curves that are obtained from a calibrated spectrometer.

For most of the data shown herein, the UV light is produced by a pulsed Xenon-filled flashlamp. Typically, the UV light in the spectral range of 210-310 nm comprises approximately 16 to 25%, and UV light in the spectral range of 200-400 nm comprises approximately 40% of the pulsed light emitted in the spectral range of 200-854 nm by the flashlamp.

Microbicidal Efficacy Testing

The ME is typically portrayed as a 'kill curve'. This curve is a plot of the "Log Kill", the logarithm of the surviving fraction of the initial challenge population, as a function of UV light fluence or BDS concentration. The fluence is defined as the time-integrated UV energy in the spectral range 210-310 nm per unit area that is incident on the surface. Typical values are in the range of 0-300 $mJ/cm^2$. The "Log Kill" is the $\log_{10}(N/N_0)$, where N is the surviving population recovered and $N_0$ is number recovered from the initial population of the challenge microbial organism. A value of $\log_{10} N/N_0=-6$ corresponds to a reduction of the challenge population by a factor of one million, i.e., $N/N_0=10^{-6}$.

In the ME tests, the BDS is applied for a specified time, typically 1 minute, and then the light is applied, typically for 1 to 5 seconds. Immediately after the application of the light, a neutralizing solution is applied to the treated sample so that the disinfection processes are stopped. In this way, the residual effect of the BDS is avoided so that a valid kill curve can be obtained. The ME of the BDS alone with a contact time of one minute corresponds to the zero fluence point on the kill curve. The ME of the BDS alone as a function of time is obtained by varying the contact time prior to neutralization. This has also been measured (data not shown).

Recovery is an important issue in microbicidal efficacy testing, and it is especially important with test object size scaling. Testing progressed from small scale laboratory tests, to larger panels (6 in×6 in or 1 ft×1 ft). For test panels up to 12" in size, a total wash with 'stomaching' in a Stomacher device and a filter concentration step lead to very high recovery on most materials and for most challenges. Notable exceptions are MS2 phage on concrete. The low recovery for phage on concrete has effectively obviated that particular assay. For panels larger than 12" and full scale test objects, such as vehicles and offices, test coupons are used so that good recovery is obtained.

The number of viable organisms is measured with an assay comprising sampling, serial dilution (by decades), plating on appropriate growth media, incubation/growth for approximately 18-24 hours, and enumeration of CFUs (for bacteria) or PFUs (for viruses). The limit of detection (LOD) is set by the initial challenge number in a sample aliquot, the recovery fraction, and the dilution level that yields a plate count of 20 to 200 or more countable units. The number in the sample aliquot depends on the size of the aliquot and the recovery rate as well as the initial concentration of the inoculum. Typically, the LOD is on the order of 5 to 7 logs for an initial challenge of $10^8$ organisms on most materials, for which the recovery rates, typically, are in the range of 1-100%.

High-Throughput 'Spot' Microbicidal Efficacy Testing

Figure 1:
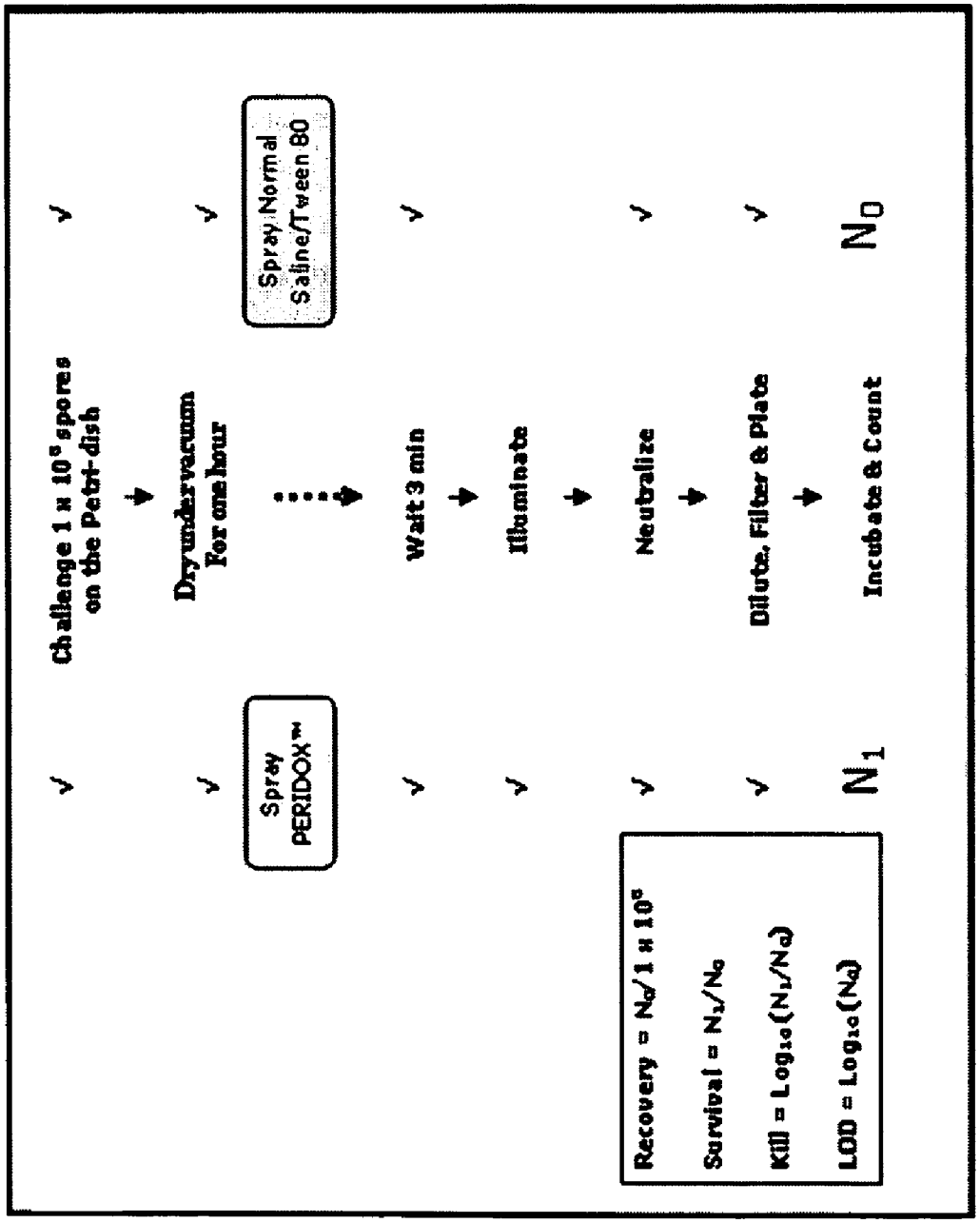
FIG. 1. Scheme for Determining the Microbicidal Efficacy of the microbicidal composition, PERIDOX™. The boxes on the left show how the data are processed.
Figures 2A, 2B:
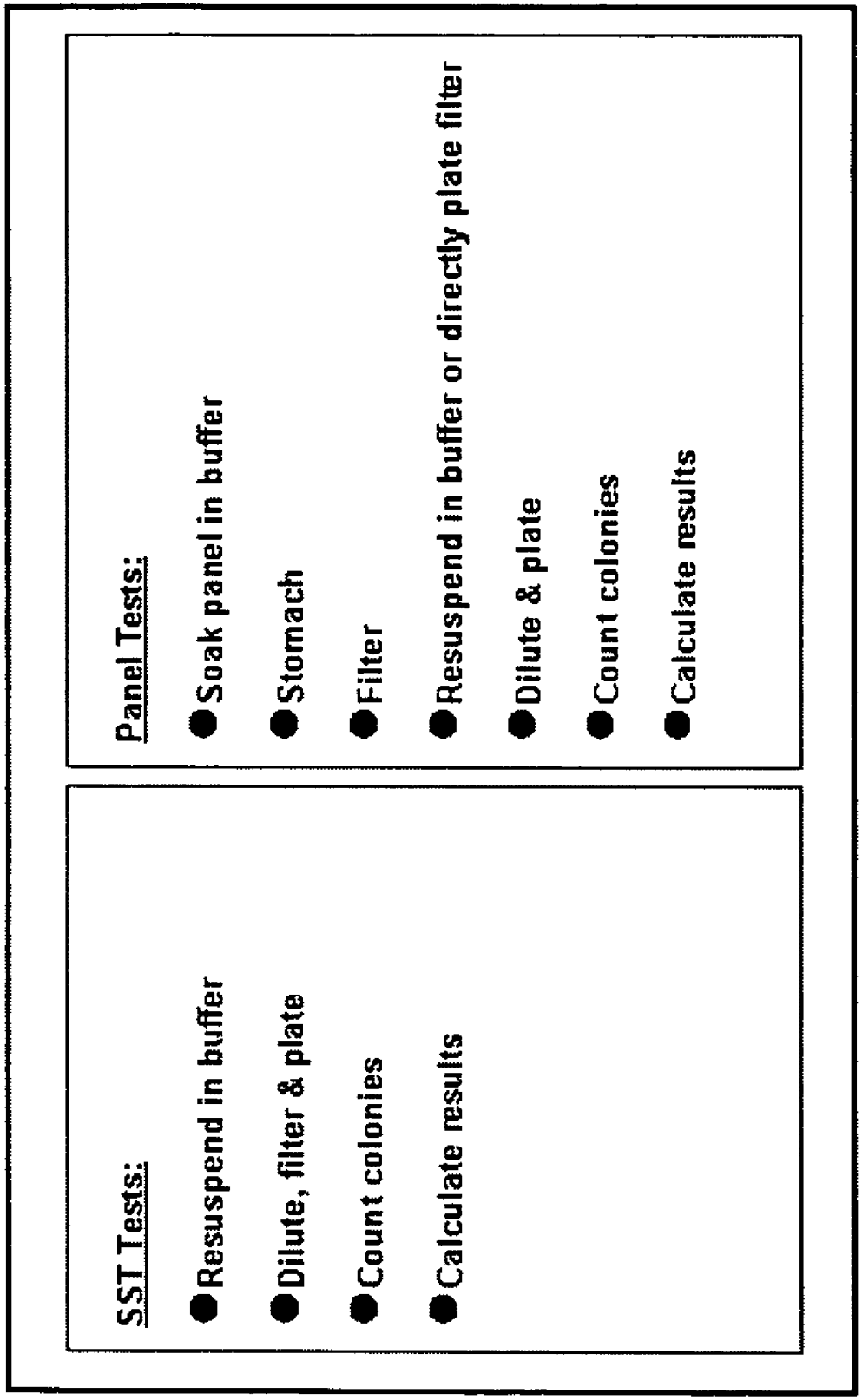
FIG. 2. Sample Processing in the SST method (FIG. 2A) vs. Full Scale Panel Tests (FIG. 2B).

'Spot' tests (FIG. 2A) are performed for photosensitizer optimization and for comparative studies. These tests follow the general scheme presented in FIGS. 1 and 2, and are performed when the objective is to compare the ME between alternative formulations or changing parameters. These tests are rapid and relatively inexpensive, but the LOD is ~5-6 logs. Typically, these tests use a challenge of ~$10^7$ to $10^8$ spores, viruses, or cells. The challenge density is typically two orders of magnitude or more greater than the spatially averaged challenge density anticipated for an incident involving a release of pathogenic agent. The challenge is deposited on the lid of a polystyrene microtiter plate and spread to fill the entire well. The challenge is dried in a 37° C. incubator for 10 to 30 minutes. BDS (100 μm layer) is added, spread over the dried spot, and allowed to stand for a defined time, usually 1 minute. The samples are then illuminated with a pre-determined amount (fluence) of UV light. Immediately after illumination, half of the sample is removed by pipetting and transferred to a buffer solution containing neutralizing solution (NS) to stop the reaction. Samples are then processed by serial dilution and plating. Colonies are counted and recorded, and survival is calculated (FIG. 1).

Biological Panel Tests

As a laboratory test scale-up in test object size, panel tests (FIG. 2B) were performed on 1 ft$^2$ (1 ft×1 ft, approximately 0.09 m$^2$) panels of materials, which are commonly used in buildings and equipment. Examples are painted drywall, carpet, ceiling tile, plastics, metals, concrete, and chemical agent resistant coating (CARC) painted steel. Typically, ~$10^{10}$ spores or viruses are 'painted' on one side and dried for 10 to 30 minutes. Electrostatic spraying of the BDS onto the test panels is conducted in a booth equipped with an exhaust vent. The spray nozzle is set up to slide along a rail located a distance of 2 ft (0.6 m) from the sample. The sprayed sample is then transferred to a mock room where it is placed on a vertical holder one foot (0.3 m) from the light wand, which is also sliding on a rail to maintain a constant distance. Four UV light detectors are placed next to the panel, one on each side (left, right, top, and bottom). The detectors are connected to an oscilloscope to measure the light output.

Figures 3A, 3B:
FIG. 3A demonstrates spreading the challenge organism over the panel (shown are *Bacillus* spores)
FIG. 3B shows the inoculated panels as they dry.

For non-absorbent materials (glass, aluminum, etc.), samples were prepared by directly pipetting the correct amount of surrogate onto the surface of the panel. A small paintbrush was then dipped into a separate container of surrogate of the same concentration, and then used to spread the sample over the surface of the panel (FIG. 3). FIG. 3A demonstrates spreading the surrogate over the panel (shown are *Bacillus* spores); FIG. 3B shows the inoculated panels as they dry. For absorbent materials (i.e., carpet, concrete), the surrogate was not pipetted on to the surface. Instead, a measured amount was directly painted onto the surface.

The general scheme of the panel testing follows FIGS. 1 and 2. Sample recovery is accomplished by placing the entire panel into a Stomacher® bag containing 1 liter of buffer and 'stomaching' for 2 minutes on the 'High' setting. The buffer is then filtered first through a 0.8 μm filter to remove particulate matter then through a 0.2 μm filter to retain the spores. When viruses are used as a challenge, host *E. coli* cells are placed into the buffer to adsorb the viruses so that they will be retained during the second filtration. The filters are then placed into a 50 ml conical test tube with 30 mls of buffer and vortexed or sonicated to remove the spores. Samples are then diluted, plated, incubated, and counted. Recovery using this method ranged from ~0.1% to 100%, depending on the challenge and the material used. Typically, the recovery rate is 20-50% for most materials.

BCO also performed panel tests as confirmation of test protocols and results for surrogates and for simultaneous pathogen and surrogate ME tests, which help to establish agent-surrogate correlations and also the ME for agent challenges. Panel tests performed at BCO are performed on smaller panels, which are 6"×6" (0.25 ft$^2$) for both surrogate and bio-agent ME panel tests. These tests use 250 ml of buffer for recovery, and only one filtration step. Because the materials tested at BCO were limited to those which do not produce particulate matter upon 'stomaching' (aluminum and butyl rubber), the 0.2 μm filter was used. Prior to filtration, samples were removed for direct plating, and then the remaining buffer was filtered and the filter was placed directly on to the Petri dish for overnight incubation. Recovery using this procedure was close to 100%.

Biological Test Strips

Biological test strips were used in a variety of test venues and test conditions to demonstrate the ME of BDS and its use as a disinfectant and photosensitizer. These tests included Controlled Environment Tests, which were performed at BCO, laboratory Vapor Tests, and a Field Test performed at the Dugway Proving Ground, UT. For the Controlled Environment Tests, the test strips are efficacy assays that determine the ME dependence on temperature, relative humidity, and wind, and large test panels are used that approach the scale of full size objects. For the Controlled Environment Tests, 4 ft square (16 ft$^2$) panels were decontaminated, and ME was measured by placing test strips at random locations on the panel. The panels were made of latex painted drywall and the test strips were made of the latex painted paper cladding typically used on drywall. The test strips were inoculated with spores (at an average density of $10^{10}$/m$^2$) and stapled on to the panel. Following treatment, the challenge on the test strips was recovered by immersion in buffer and vortexing or sonication.

For the vapor chamber tests, Post-It® flags (11.9 mm×43.2 mm) were inoculated with the amount of organisms required (typically $10^7$ to $10^9$). Recovery was performed by vigorous vortexing of each test strip in 2 mls of buffer.

Data Analysis

Each experiment was performed in triplicate, except for a few special cases as indicated in the text. Averages and standard deviations are calculated in cases where countable colonies were recorded [when growth was either 'too numerous to count' (TNTC) or 'no growth' (NG)]. In cases where no detectable growth was found, the data are represented by an asterisk (*) plotted at the value of the limit of detection (LOD) for the experiment. Statistical analysis was performed either in Microsoft® Excel or JMP® Statistical Analysis software (SAS, Cary, N.C.). Specifics for each analysis are described in the corresponding figure legend. No data were excepted from the analysis or plots, although test sequences in which controls were obviously compromised, e.g., contaminated with vapors, unintentionally, have been 'thrown out', even though the ME results may have been consistent with other tests.

Neutralization of Disinfecting Action

Figure 4:
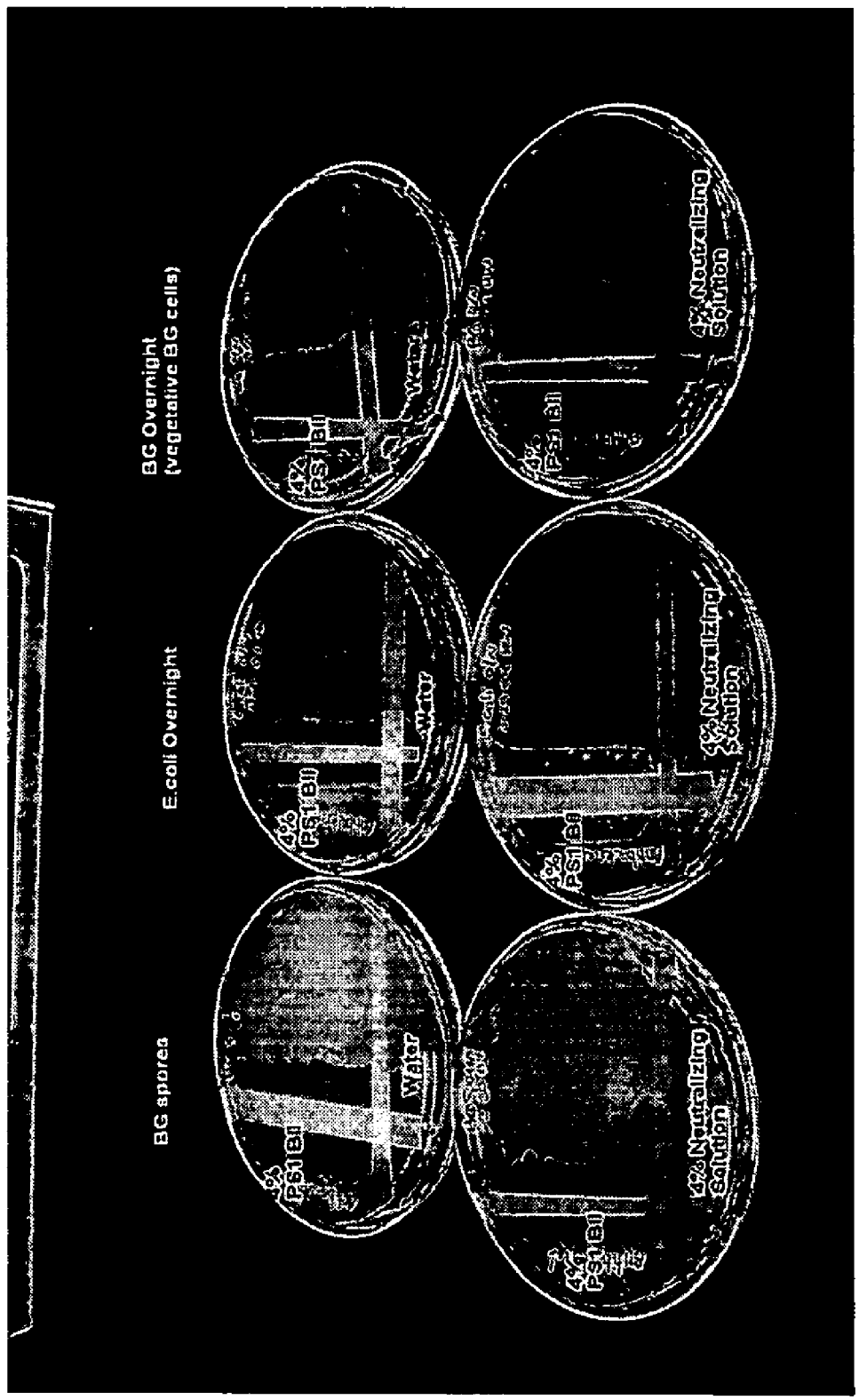
FIG. 4. Neutralization of Anti-microbials. Neutralization of BDS (labeled as "PS1'BII") is shown for vegetative bacteria and spore inocula. The vertical filter strip was soaked in BDS and the horizontal filter strip was soaked in neutralizing solution. Data were acquired at CET.

Tests were performed to verify that the microbicidal action of the various compositions was neutralized prior to assay by plating, incubation, and enumeration. FIG. 4 demonstrates how a neutralization solution is tested. First, a lawn of cells is plated. A strip of filter paper soaked in the decontaminant is laid across the lawn in one direction and another strip soaked in neutralizer is laid across the lawn in another direction. Following overnight incubation of the plates, one can observe a zone of inhibition in areas where the decontaminant was not neutralized. In contrast, at the intersection of the two strips (where the decontaminant is neutralized), the cells grow.

Several attempts were made to compare the ME of BDS to peroxide and quaternary ammonium-containing compositions. However, all efforts at neutralizing the quaternary ammonium-containing compositions failed. The use of DE neutralizing broth or sodium thiosulfate as a neutralizer was recommended (J. Rogers, BCO). These treatments neutralize oxidants and are included in the neutralizing solution used to successfully neutralize BDS, but it failed to neutralize the peroxide/quaternary ammonium compositions. Lecithin, which is used to neutralize quarternary ammonium compounds (included in Leethan broth) was also tried but failed. The failure to neutralize such compositions makes such assays meaningless. In contrast, the demonstration that BDS can be neutralized successfully supports the validity of the microbicidal efficacy testing reported herein.

Results

Representative results of the testing are described herein in the following examples. Data and results are shown in FIGS. 5-24.

EXAMPLE 1

In this example, BDS is shown to be a broad spectrum microbicide. The formulation for this example, referred to as 4% BDS, is:

| Formula | Material |
|---|---|
| 4% $H_2O_2$ | $H_2O_2$ 30% |
| 0.2% PAA | PAA 32% |
| 0.1% PVP | PVP (10K) |
| 0.1% OC-40 | OC-40 |
| Balance | Water |

Table V lists test organisms and ME (kill level) for the treatment with BDS and BDS activated by high UV content light. The results show the sensitivity of various microorganisms to these treatments. For this example, the challenge level was ~$10^{11}$/m². High level disinfection is demonstrated.

TABLE V

ME of BDS on a Variety of Microorganisms

| TYPE | SURROGATE/ AGENT | KILL LEVEL (Logs) | |
|---|---|---|---|
| | | BDS | BDS & UV |
| Spore | B. atrophaeus | 4.5* | 7.0* |
| | B. anthracis | 3.0 | 6.3 |
| Gm+ vegetative | B. atrophaeus | 4.5 | 5.0* |
| | S. aureus | 6.2* | 6.0* |
| Gm− vegetative | E. coli | 6.2* | 6.0* |
| Virus | MS2 | 1.8 | 6.0 |

Notes:
BDS, Biological Decon Solution was used at 4%; UV, ultraviolet light was used at 90 mJ/cm²; challenge level was $10^8$ organisms at a density of ~$10^{11}$/m². Contact time for BDS was 1 minute under both treatments.
*No survivors were detected (the number represents the LOD). The data for each organism was obtained in separate experiments. The data for MS2, S. aureus, B. atrophaeus, and B. anthracis were obtained by BCO; the data for E. coli were obtained by CET.

Correlation between B. atrophaeus and B. anthracis

It can be seen in Table V that ME for B. atrophaeus and B. anthracis differs for BDS treatments both with and without UV light. These experiments were performed with spore preparations that were available but had been grown under different conditions (i.e., not grown specifically for a comparison of ME for both strains). The growth conditions for spores do affect the resistance of the spores to a particular treatment. Here, the B. anthracis spores were grown in Leighton-Doi medium while the B. atrophaeus spores were grown in Modified G medium. Subsequent experiments conducted at CET demonstrated differences in growth kinetics and microbicide resistance between B. atrophaeus strains grown in the two different media. Subsequent studies conducted by MRI demonstrate that when the two strains are grown in the same medium (Schaeffer's), similar ME is observed in both (FIG. 11).

EXAMPLE 2

The Biological Decon Solution and High UV Content Light Act Synergistically

Figure 5:
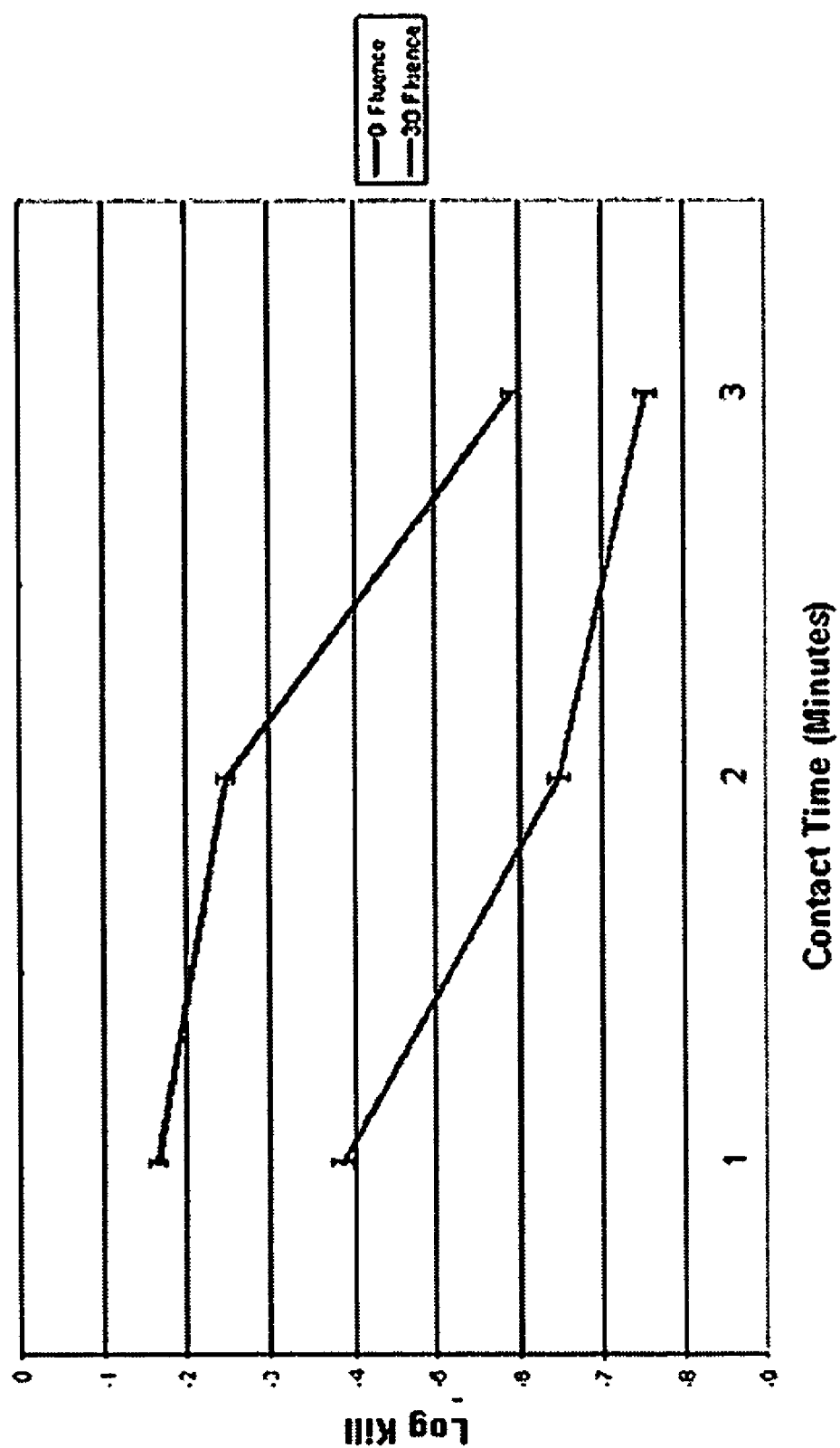
FIG. 5. Comparison of the efficacy for the EDS process, i.e., PERIDOX™ plus high UV content light (lower curve) and PERIDOX™ Only (upper curve) against *B. subtilis* Spores as shown in tests performed by the SST Method.

A comparison of efficacy for the EDS process, i.e., PERIDOX™ plus high UV content light (lower curve) and PERIDOX™ Only (upper curve) for the inactivation and killing of B. subtilis Spores shows that the BDS and high UV content light act synergistically. The data shown in FIG. 5 are the results of tests that were performed by the SST Method. A challenge of 7.95×10⁷ to 1.07×10⁸ spores/Petri dish was spread into an area of 3.5 cm in diameter on a 6 cm in diameter Petri dish and dried for 1 hour under vacuum. Dried spores were treated with 4% PERIDOX™ prepared with 200 ppm AOAC hard water as the diluent. After contact times, samples were illuminated with a fluence of 30 mJ/cm² from the CET light source, or not illuminated. Three contact times (1, 2, and 3 minutes) were used. Three samples for each contact time were tested, except 10 samples were tested for the 3-minute contact time for EDS treated group. The recovery rate was 63.82-93.67%. LOD=7.83-7.91 logs.

Similar experiments were conducted with S. aureus bacteria (FIG. 6). The experiments compared the BDS to hydrogen peroxide (HP) as a photosensitizer for killing bacteria. S. aureus cells ($10^8$) from an overnight culture were spread at an average density of ~8×$10^{10}$ CFU/m² and dried. Ultra pure water, 1% HP, or 1% BDS (in FIG. 6: A, B, and C, respectively) was added. Samples stood for 1 min before illumination at the fluences shown. The asterisk (*) denotes the level of detection (LOD) in samples showing no growth. Error bars and mean error bars are shown (the curve connects the means). Statistics were computed using the LOD as the value for * when more than one value was obtained. Recovery~1%; n=2 for each set of conditions. Data were acquired at BCO.

In FIG. 6, data are shown for *S. aureus* treated by (A) UV only, (B) UV plus HP, and (C) UV plus 1% BDS. It is seen that BDS and BDS with high UV content light are superior in microbicidal efficacy and achieve killing to the level of detection.

Figures 6A, 6B, 6C:
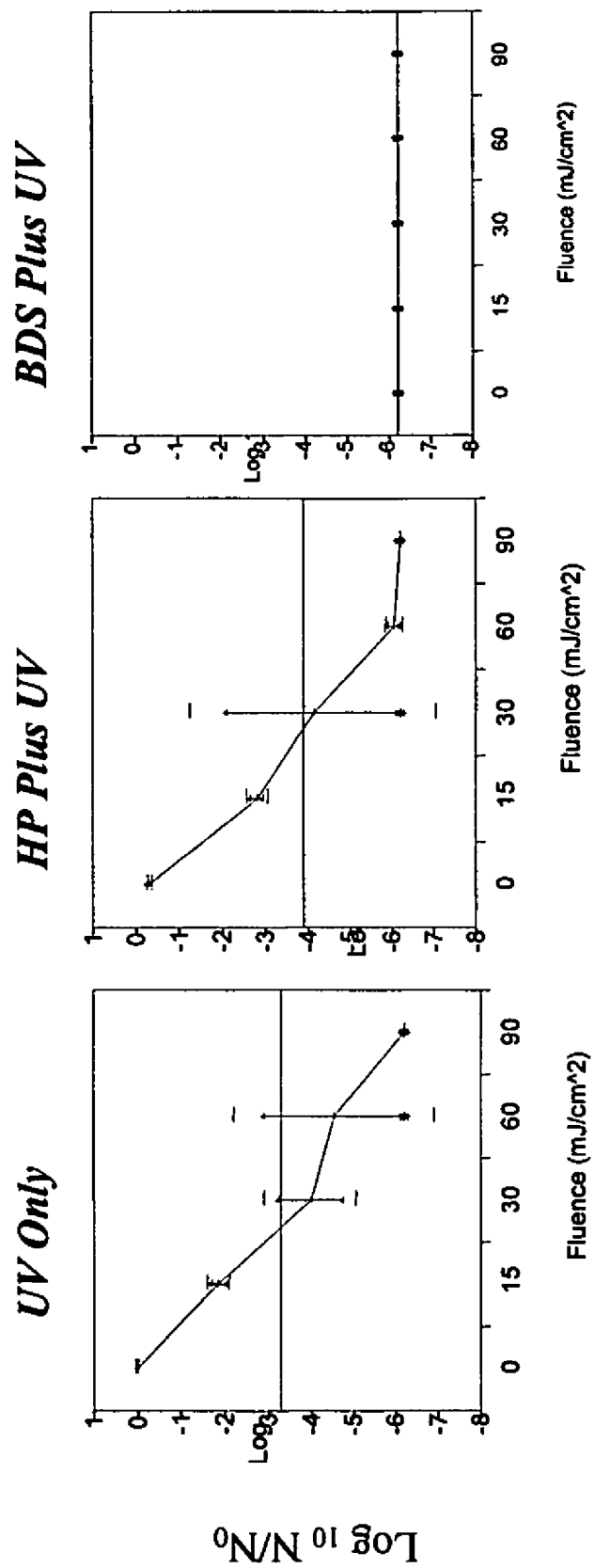
FIG. 6. Comparison of the BDS to hydrogen peroxide (HP) as a photosensitizer for killing bacteria. Data are shown for *S. aureus* treated by (A) UV only, (B) UV plus HP, and (C) UV plus BDS.

It has been known for some time that UV light and hydrogen peroxide act synergistically to kill bacteria. That effect is seen in FIG. 6, where *S. aureus* cells were exposed to UV alone (FIG. 6A) or UV plus hydrogen peroxide (FIG. 6B). The combination of BDS and UV (FIG. 6C) shows a much greater level of kill (to the LOD). It is found that BDS at a concentration of 1% kills the bacteria even without UV. At lower concentrations of BDS, the synergistic effect of BDS plus the UV is observed (data not shown).

In a similar test, 2% BDS was used to kill MS2 bacteriophage. This concentration is half the concentration for general use with the EDS. Complete killing to the level of detection (approximately 6 logs) is obtained at a fluence of approximately 90 mJ/cm$^2$ for a challenge level of 1×10$^8$ PFU at a density of 8.5×10$^4$ PFU/mm$^2$. With treatment by light-only, approximately 4-logs of killing is obtained.

EXAMPLE 3

Microbicidal Efficacy Tests with 4% BDS

In this example, 4% BDS is used to kill spores of the bacterium *B. globigii* (Bg, also called *Bacillus atrophaeus*) (FIG. 7) and also a Gram negative vegetative bacterium, *E. coli* (FIG. 8), and spores of the bacterium *B. globigii* (Bg) (FIG. 7). The ME kill curve for Bg is shown in FIG. 7 as a function of the UV light fluence for comparative treatments of *Bacillus globigii* (Bg) spores. In FIG. 7A only light is applied; in FIG. 7B light plus 4% hydrogen peroxide are applied; and in FIG. 7C 4% BDS photosensitizer plus light are applied. The asterisk (*) denotes the level of detection where no colonies were produced. All test populations shown in FIG. 7C were killed at least to the level of detection (over 6 logs). The challenge level is 1×10$^8$ CFU at a density of 8×10$^4$ CFU/mm$^2$ The ME kill curve for *E. coli* is shown in FIG. 8 as a function of the UV light fluence for comparative treatments. In FIG. 8A only light is applied; in FIG. 8B light plus 4% hydrogen peroxide are applied; and in FIG. 8C 4% BDS photosensitizer plus light are applied. The asterisk (*) denotes the level of detection where no colonies were produced. All test populations shown in FIG. 8C were killed at least to the level of detection (over 6 logs). The challenge level is 1×10$^8$ CFU at a density of 8×10$^4$ CFU/mm$^2$. BDS and BDS plus high UV content light achieve 6-logs killing to the LOD.

EXAMPLE 4

ME for Killing Virus as a Function of BDS Concentration

Figure 9B:
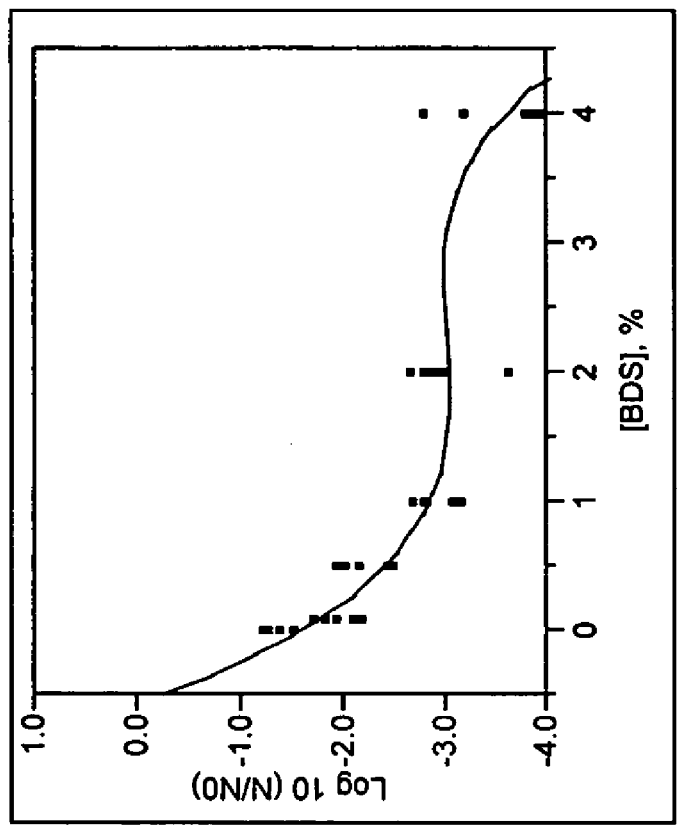
Figure 9A:
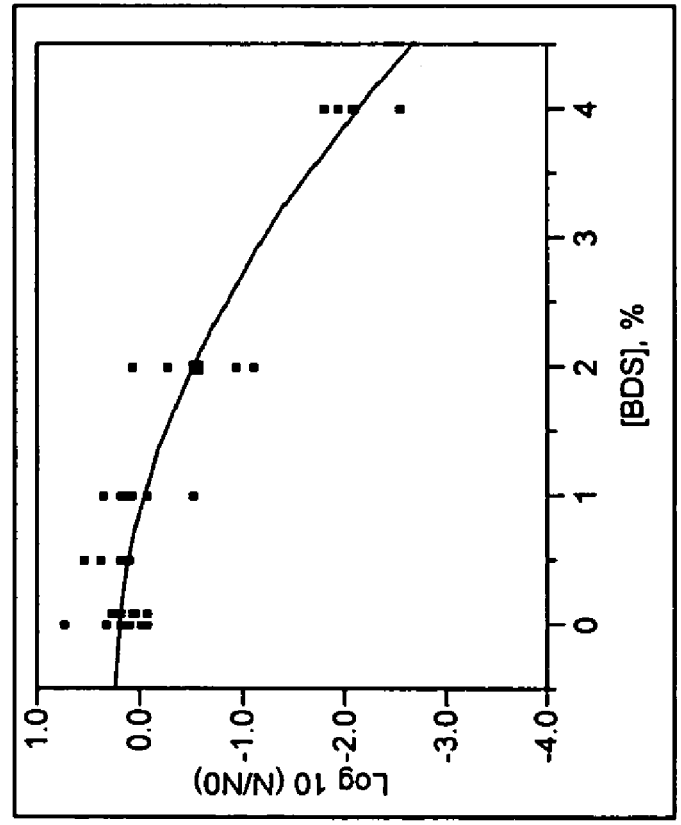

Tests were performed to determine the ME as a function of BDS concentration for killing MS2 bacteriophage. FIG. 9 shows the results of the tests. Kill curves are shown for treatment of bacteriophage MS2 by BDS alone (FIG. 9A) and by BDS with high UV content light (FIG. 9B). In this example, the density of phage per unit surface area was 10$^{12}$ PFU/m$^2$, which is four orders of magnitude (10,000 times) higher than a typical challenge level of 10$^8$/m$^2$, which is anticipated for a release of pathogens. The high challenge level was used so that the kill curve could be better observed in the 0-4 log range. The shape of the non-illuminated data set (FIG. 9A) has a shoulder, suggesting multiple hits are required for killing the phage. On the illuminated data set (FIG. 9B), exponential killing is observed at the beginning of the curve. This behavior is characteristic of a greater amount of toxic molecular species present following illumination. The tail of the curve in the illuminated set (FIG. 9B) levels off, suggesting that the phage sample that was used had clumps, which are more resistant to killing. This phenomenon occurs when high challenge levels are used. The spots were treated with varying concentrations of BDS alone for 1 minute, FIG. 9A, or also treated with 90 mJ/cm$^2$ UV light. FIG. 9B, followed by neutralization, dilution and plating onto *E. coli* host cells. For each set of conditions, n=6. For curve in FIG. 9A, r$^2$=0.90; for curve in FIG. 9B, r$^2$=0.83. Data were acquired at CET.

In the absence of BDS, 90 mJ/cm$^2$ of UV light reduces the phage population by approximately 1.6 logs (FIG. 9B); in the absence of UV/light activation, 2% BDS shows less than 0.5 logs of killing (FIG. 9A). If the effects of light (activation and killing) and BDS were additive, the expected level of kill for 2% BDS plus 90 mJ/cm$^2$ of UV would be two logs. However, in practice, the treatment results in three logs kill, i.e., the two act synergistically.

FIG. 9 also shows that both in the presence and absence of light activation, killing increases as the concentration of BDS is increased. For the photosensitized killing, this trend in the dependence on concentration begins to reverse when the concentration of hydrogen peroxide exceeds 6% (data not shown).

EXAMPLE 5

ME for killing *Bacillus anthracis* Spores

The ME of BDS for killing dried *Bacillus anthracis* spores was measured as a function of fluence using the "Spot Test" method (see Materials & Methods above). FIG. 10 shows greater than 6 logs of kill achieved with a fluence of 30 mJ/cm$^2$ (~1 second of exposure). Ba spores (10$^8$) were spread and dried. The average density of spores was 3.3×10$^{11}$ CFU/m$^2$. One hundred (100) µl of 4% BDS ('PS1'B') was added. Samples stood for 1 minute before illumination at the values shown. One hundred (100) µl of NS was added and 10 µl of sample was removed and serially diluted. Samples from each dilution were plated on blood agar and incubated at 37° C. overnight. Colonies were counted and data were computed as described in Materials & Methods. Data acquired at BCO. Recovery=18% and n=11.

Additional ME testing has established a correlation for results with Ba and Bg. Data in FIG. 11 show that Ba and Bg, when grown and prepared by identical methodology, have the same response to a given treatment, e.g., treatment with BDS or treatment with BDS plus high UV content light. In this data (obtained at MRI), it is seen that a greater than 6-log reduction is obtained with 4% BDS and 15 mJ/cm$^2$ fluence.

EXAMPLE 6

Panel Tests

The BDS and BDS plus high UV content light activation (the EDS treatment process) is effective on a variety of materials. Scaled-up ME tests were performed on thirteen (13) different materials of 1 ft$^2$. Each material was tested with 4% BDS alone and EDS treatment. The EDS treatment was performed with a full prototype EDS unit. All of the tests done previously that involved BDS plus high UV content light were done with the sample on the benchtop underneath a xenon flashlamp on a stand and BDS as a photosensitizer was applied with a pipettor. The panel tests more closely resemble a decontamination operation that would be performed in the field. Thus, electrostatic spraying was being used for the first time in an efficacy test of the BDS and EDS treatments. Other conditions that were different between the two test types included the distance of the lamp from the panel (24 inches rather than 12 inches), vertical orientation of the panel, motion on the part of the operator (both in the application of the BDS and the light), longer contact time (15 minutes) and an attempt at full recovery of the sample.

FIG. 12 summarizes the overall outcome of the tests on the 1 ft square panels by treatment. It can be seen that EDS performs better than BDS alone and the results are close but statistically significant. Typical recoveries were 20-50%, except for ceiling tile, which was around 6%, and concrete, which was around 0.1%. Because recovery was so low for ceiling tile and concrete, those data were omitted from the comparative analysis. Each panel contained $10^{10}$ dried Bg spores. For the EDS treatment, the UV fluence was ~90 $mJ/cm^2$. Recovery was 20 to 50%. For each material, the number of replicate tests is n=3. Data acquired by CET.

Panel testing was performed to determine the ME for killing dried Ba spores on larger scale size surfaces. Comparative testing was performed on Ba and Bg spores at BCO. These panels were 6 inches by 6 inches in size. The challenge on each 6 inch×6 inch panel was $1.9×10^9$ CFU/ml, and sample recovery was 64%. Table VI shows the results of these tests performed on aluminum and butyl rubber using BDS alone and with high UV content light. For comparison, the ME of bleach on panels was performed side-by-side on Bg. Results of the tests with dried Bg spores are shown in FIG. 13. In FIG. 13 the BDS+light treatment (labeled "PS+UV") is seen to be superior to either BDS alone (labeled "PS") or bleach. From Table VI, it can be seen that there is not an exact correlation between the surrogate and the pathogen (which were grown under different conditions). The EDS treatment is more effective for the time frame of this example (1 minute contact time) than BDS alone. However, both are more effective than bleach.

TABLE VI

ME of Biological Decon Solution on Panels
(Bg = *B. atrophaeus*; Ba = *B. anthracis*)

| ORGANISM | MATERIAL | LOG KILL | | |
|---|---|---|---|---|
| | | BDS & UV | BDS | BLEACH |
| Bg | Aluminum | 6.0-8.0 | 4.2-5.8 | 1.5-3.0 |
| | Rubber | 5.0 | 4.5 | 0.3 |
| Ba | Aluminum | 5.2 | 1.0 | |
| | Rubber | 4.4 | 1.2 | |

Data were acquired at BCO.

The EDS treatment process is effective under a variety of environmental conditions. The objective of the Controlled Environment tests was to find out how wind, relative humidity and temperature affect decontamination of biological agents. These tests were conducted at BCO in a stainless steel paneled walk-in incubator. An EDS prototype unit was used for spraying and illuminating the samples. Bg spores were painted onto 1 inch by 2 inch coupons of latex painted drywall cladding tacked at random locations onto a 4 square foot panel of latex painted drywall. Data for temperature and wind are presented in Table VII. A small but significant reduction in ME is seen in the samples treated at 15° C. in the presence of wind. Varying the relative humidity had no significant effect on ME (data not shown).

TABLE VII

Controlled Environment Test Results

| SAMPLE LOCATION | T = 15° C. − WIND | | | T = 15° C. + WIND | | | T = 30° C. − WIND | | | T = 30° C. + WIND | | |
|---|---|---|---|---|---|---|---|---|---|---|---|---|
| | A | B | C | A | B | C | A | B | C | A | B | C |
| 1 | 7.0 | 6.3 | 5.7 | 5.7 | 4.9 | 3.0 | 6.5 | 5.9 | 6.3 | 5.3 | 6.1 | 5.6 |
| 2 | 6.5 | 6.7 | 6.4 | 3.2 | 6.1 | 6.1 | 6.6 | 5.9 | 6.2 | 5.8 | 6.4 | 6.1 |
| 3 | 6.2 | 6.7 | 6.1 | 5.7 | 3.1 | 4.0 | 6.5 | 6.4 | 6.0 | 5.6 | 5.1 | 6.9 |
| 4 | 6.4 | 6.9 | 6.4 | 2.8 | 3.0 | 4.6 | 5.4 | 5.3 | 6.3 | 5.7 | 5.6 | 5.9 |
| 5 | 7.2 | 6.1 | 6.5 | 3.0 | 3.4 | 3.1 | 5.1 | 6.2 | 6.0 | 5.6 | 6.1 | 5.1 |
| 6 | 6.3 | 6.6 | 4.8 | 5.6 | 6.3 | 3.8 | 5.5 | 4.3 | 5.0 | 5.9 | 5.8 | 5.9 |
| Average | 6.6 | 6.6 | 6.0 | 4.3 | 4.5 | 4.1 | 5.9 | 5.7 | 6.0 | 5.7 | 5.9 | 5.9 |

Data were acquired at BCO.

The performance of EDS treatment process was also demonstrated in a field test in desert conditions. The EDS was tested extensively for reliability, operability and mainability at the Dugway Proving Grounds where temperatures averaged 110° F. and humidity averaged 11%. Sustained winds exceeded 15 mph. The BDS performed well under these conditions, remaining liquid for one and one-half to two minutes following spraying Bradley Infantry Fighting Vehicle.

EXAMPLE 7

Comparison of ME for BDS Formulations with 2 Different Phosphate Esters

Tests were performed to determine the comparative ME of 4% BDS formulated with OC-20, an ethoxylated phosphate ester of nonyl phenol and 4% BDS formulated with OC-40, a phosphate ester of tridecyl alcohol ethoxylate. The OC-20 was initially selected as a photo-active surfactant for BDS and used successfully. However, it was learned that OC-20 may not be as environmentally desirable because of its R-terminal aromatic group. Consequently, OC-40 was selected as an alternative. The results of the comparative tests are shown in FIGS. 14, 15, and 16, which show the ME for BDS and BDS plus high UV content light for killing *E. coli*, MS2 bacteriophage, and dried Bg spores, respectively. The typical standard deviation is approximately 0.5 logs of kill. Thus, it is seen that OC-20 and OC-40 have practically the same ME for killing *E. coli* and MS2, but OC-40 is clearly superior by 2 logs for killing dried *Bacillus* spores on a surface by BDS treatment without light activation.

EXAMPLE 8

DNA Destruction

Treatment by BDS with subsequent illumination by UV light effectively produces irreversible DNA damage in vegetative and spore DNA.

It is a well-known fact that UV light causes reversible damage in the form of pyrimidine dimers (including T-T-dimers) to DNA in living cells. This type of lesion involves formation of a covalent bond between two adjacent pyrimidine bases but leaves the DNA backbone intact. Two repair systems for pyrimidine dimers, known as 'light repair' and 'dark repair' are ubiquitous in living systems (from bacteria to humans) and are capable of reversing the damage. DNA containing T-T dimers can be assayed in vitro by digestion with endonuclease V, which cleaves DNA specifically at the site of T-T dimers.

To demonstrate the formation of T-T dimers, four different treatments were applied to a challenge of $10^8$ vegetative Bg cells (as labeled in FIG. 17). Four different treatments were applied to a challenge of $10^8$ vegetative Bg cells (as labeled). The samples were neutralized after the treatment and DNA was extracted with a bacterial genomic DNA kit from Sigma. The DNA was either digested (+) or not digested (−) by T4 Endonuclease V for 1 hour. The DNA was electrophoresed on a 1% agarose gel. FIG. 17 shows that UV light alone produces DNA with T-T dimers, which results in digestion by endonuclease V and that this damage increases as fluence is increased.

FIG. 18 shows that EDS destroys nucleic acid compounds, in particular, DNA. BDS or UV alone result in insignificant destruction of DNA, and neutralized PS (PS+NS) shows no DNA destruction. However, it is seen that the lane marked EDS (BDS+UV) shows thorough destruction of DNA without the addition of endonuclease V. The samples were neutralized after the treatment and DNA was extracted with a MOBIO UltraClean™ Microbial DNA isolation kit. The extracted DNA was electrophoresed on a 1% agarose gel. M, molecular weight markers.

FIG. 19 shows that the irreversible destruction of DNA depends on the sequence of BDS and UV treatment (i.e., BDS must be added first; "PS"=BDS). Thus, BDS acts as a photosensitizer. Four different treatments were performed, which varied according to whether and the order in which BDS (PS) or UV treatments were applied. The challenge was $10^8$ Bg spores. The samples were neutralized after the treatment and DNA was extracted with a MOBIO UltraClean™ Microbial DNA isolation kit. The extracted DNA was electrophoresed on a 1% agarose gel.

FIG. 20 shows the dependence of ME on the UV content of the light. Five different treatments were applied to a challenge of $10^8$ *B. atrophaeus* spores (as labeled above in FIG. 20). FS refers to the full spectrum of the light source. The samples were neutralized after the treatment and DNA was extracted with a MOBIO UltraClean™ Microbial DNA isolation kit. The extracted DNA was electrophoresed on a 1% agarose gel. It is seen that UV-A (320-400 nm), UV-B (280-320 nm), and UV-C (<280 nm) each contribute to the destruction of DNA.

EXAMPLE 9

ME of Vapor

The microbicidal efficacy of the BDS for disinfection by vapor was demonstrated in a vapor chamber (FIG. 21). The ME of the BDS vapor was examined while varying three parameters: temperature, challenge level, and BDS (not vapor) concentration applied to the chamber. Bg spores were placed on a test strip at the indicated challenge level and dried before exposure to the BDS vapor. Chamber volume was 902.6 $cm^2$. Liquid BDS was placed in the bottom of the chamber and the spore test strips were attached to the top of the chamber. The spores were exposed to the vapor for 10 minutes at the indicated temperature. Challenge is reported as CFU/$m^3$ of vapor. Sample recovery was 75-85%; n=2. Data were acquired at CET (see FIG. 21). The spores ($10^9$) were exposed to the vapor for 10 minutes at the indicated temperatures: (top) 22° C.; (bottom) 37° C.

FIG. 21 shows that ME is greater at higher temperature and higher BDS concentration. The increased kill at the higher challenge levels is an artifact of the experimental method. In this experimental system, the limit of detection increases as the challenge level increases and at 22° C. (FIG. 21A) the maximum measurable kill is reached at a concentration of 4% BDS (at concentrations of 4% and higher no survivors were detected). At 37° C. (FIG. 21B), the maximum is reached at 2%. Sample recovery was 75-85%; n=2. Data were acquired at CET.

EXAMPLE 10

Comparison With Other Anti-microbials

Comparative tests between 4% BDS and other microbicides has been performed. The activity of BDS alone (FIG. 22A) or with UV illumination (FIG. 22B) was compared to a commercial product, PeraSafe™, which contains the active ingredient hydrogen peroxide. PeraSafe™ has not been formulated or marketed as a UV photosensitizer. The challenge was $10^7$ PFU or CFU/spot ($10^{11}$ PFU or CFU/$m^2$). Both PERIDOX™ and PeraSafe™ were used at a concentration of 4% hydrogen peroxide for a contact time of 1 minute. Fluence in FIG. 22B was 60 mJ/$cm^2$. Recovery~10%; n=2 or 3.

FIG. 22 shows that BDS has greater overall efficacy than PeraSafe™. PeraSafe™ was tested at a concentration of 4% (even though manufacturer's recommendations are for a 1.6% solution) to allow for a balanced comparison. BDS clearly has greater ME than PeraSafe™. The asterisk in the figure means that no survivors were detected (data points represent the limit of detection for the trial). Data were acquired at CET.

Likewise, Virkon® (a blend of peroxygen compounds including triple salt of potassium monopersulfate, surfactant, organic acids and an inorganic buffer system) was tested at a concentration of 4% and the results are presented in FIG. 23. The challenge was $1\times10^7$ organisms/spot ($10^{11}$ organisms/$m^2$). Both BDS ('PS1'B' in the figure) and Virkon® were used at a concentration of 4% HP for a contact time of 1 minute. Fluence was 60 mJ/$cm^2$ Reactions were neutralized before dilution and plating. Colonies or plaques were counted and data were computed as described in Materials & Methods. Statistics were computed using the LOD as the value for *. Recovery~10%; n=2; LOD was ~6 logs. Data were acquired at CET.

BDS showed better performance than Virkon® even though the manufacturer's recommendation is to use a 1-2% working solution. At this concentration, ME for MS2 is similar for the two solutions, but BDS is clearly more effective on spores. It is not surprising that the high UV content light made no difference in the performance of the Virkon® since this solution was not designed to be a photosensitizer. UV will not necessarily be synergistic or even additive unless the solution is designed for use as a photosensitizer.

Further tests were performed by BCO for a comparison of BDS and bleach. Tests were performed with two replicate aluminum panels. The results show a 7 log kill using EDS and only 1 log kill using bleach in the case where the contact time is 1 minute. At CET the contact time comprised a 1 minute interval after spraying, then the panel was illuminated, and then an additional contact time of 15 min was allowed before neutralizing and processing. At Battelle, they sprayed, illuminated, neutralized, and processed. This demonstrates the advantage of rapid disinfection, which results because of the synergistic microbicidal effect of BDS plus light, over traditionally used disinfectants and sanitizers such as bleach.

EXAMPLE 11

Material Compatibility

The compatibility of the BDS with a variety of materials was examined. Two types of tests were performed. One is an immersion test with 48 hour duration. The other is a repeated spray test that mimics the EDS treatment process. The spray tests comprise five cycles of spraying followed by high UV content light illumination and subsequent drying. Various material properties were examined. These included appearance, hardness, and pH change of the BDS. No significant changes in these characteristics were observed. FIG. 24 shows the average percent weight change of various materials following 48 hour immersion in BDS at room temperature. The bars represent the average of three samples. Most materials show no effects. Thus, BDS has excellent compatibility with most materials and exhibits good non-corrosive properties. The materials with the most change were paper and polymer tape (the type used to mark off crime scenes). However, it should be noted that in other tests on paper, e.g., paper printed with a laser printer and paper with a text image from a photocopier only appeared slightly wrinkled but were still readable (no streaking, running, or fading of the ink) after immersion in BDS for 28 days. Data were acquired at CET.

EXAMPLE 12

Moldicidal Efficacy

Tests of 4% concentration BDS applied to surfaces contaminated with common molds, e.g., Aspergillus niger, show microbicidal efficacy of >5 logs killing with a 10 minute contact time. Thus, BDS may be used as a means to treat mold infestations.

SUMMARY

The ME testing shows that the BDS, when used as a sanitizer, disinfectant, sterilant, or as a photosensitizer for the EDS process in which microbial species and nucleic acid compounds are destroyed, is very effective as a sporicide, bactericide, virucide, fingicide, and moldicide. Excellent results are obtained on the range of materials and smooth and textured surfaces that were tested. In nearly all cases, kill to the level of detection was obtained. In the exceptional tests, imperfect test procedures and test conditions account for apparent reduced kill. Limited and preliminary comparative ME testing shows that the EDS process and BDS are equal to or superior to competing disinfectants and decontaminants, but the EDS process and BDS also have broad spectrum ME, capability of causing irreversible damage to DNA, speed, better solution utilization/logistics, and good material compatibility in comparison with other decon solutions. It is found that the EDS process is robust against known interferences to decontamination. The BDS can be prepared with water stock of diverse quality, from ultra-pure to natural waters and seawater, without significant impact on efficacy. The BDS is also seen to have excellent compatibility with the wide range of materials, which are likely to be encountered in healthcare, industrial, emergency responder, counter-terrorism, and military settings.

It has been shown that BDS kills Gram positive and Gram negative vegetative cells, bacterial spores and bacterial viruses with high efficacy and irreversibly destroys their nucleic acids. BDS has also been shown to kill molds and fungi. The BDS shows high efficacy, alone or in combination with light, on a variety of surfaces and under a range of environmental conditions.

BDS is effective as a liquid sporicide, a photosensitizer, and a vaporous sporicide. As a photosensitizer, the BDS provides high level kill of spores (~6 logs) in a matter of seconds following UV exposure. This advantageous capability of rapid effect is ideal for tactical applications on military missions and for rapid decon in emergency and medical settings. One limitation of photochemical decontamination is the inability of the light to reach non-line-of-sight surfaces (i.e., the nooks and crannies of complex surfaces). The use of electrostatic spraying counters this limitation by a 'wrap around' effect, whereby, non-line-of-sight surfaces can be coated with the BDS. In this manner, practical, effective, and rapid disinfection can be accomplished.

The sporicidal activity of the BDS vapor can be used in a chamber to provide batch decon of small objects and sensitive equipment.

BDS can also be used as an immersion bath for the decontamination, sanitization, disinfection, or sterilization of objects.

LIST OF ACRONYMS

| | |
|---|---|
| AOAC | American Organization of Analytical Chemists |
| ATCC | American Type Culture Collection |
| Ba | Bacillus anthracis |
| BCO | Battelle Memorial Institute, Columbus, OH |
| BDS | CET's proprietary Biological Decon Solution (a.k.a. PERIDOX ™) |
| Bg | Bacillus atrophaeus |
| CET | Clean Earth Technologies, LLC |
| CFU | Colony Forming Units |
| DNA | Deoxyribonucleic Acid |
| EDS | Electrostatic Decontamination System |
| EPA | Environmental Protection Agency |
| GC-FAME | Gas Chromatography-Fatty Acid Methyl Ester |
| HP | Hydrogen Peroxide |
| LB | Luria Broth |
| LOD | Limit of Detection |
| ME | Microbicidal Efficacy |
| MRI | Midwest Research Institute, Kansas City, MO |
| N | Surviving Population |
| $N_0$ | Initial Population |
| NG | No Growth |
| NS | Neutralization Solution |
| PA | Protective Antigen |
| PAA | Peroxyacetic Acid |
| PFU | Plaque Forming Units |
| T | Temperature |
| TNTC | Too Numerous To Count |
| TSB | Tryptic Soy Broth |
| UV | Ultraviolet |

The teachings of this specification are representative examples, and as will be obvious to those practiced in the art, there are many variations in concentration and combinations of surfactants and polymers and peroxide and peracid compounds that will exhibit the photoactive behavior that enhances microbicidal efficacy.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed:

1. A microbicidal and decontaminant composition comprising:
    an aqueous solution of peroxides and peracids having equilibrium reaction products;
    an anionic photoreactive surfactant comprising a phosphate ester comprising a hydrophilic polyoxyethylene chain having a range of PEO-3 to PEO-9 and an R-terminal group selected from the group consisting of a lipophilic alkyl chain having a range of C9 to C13 and an nonylphenol; and
    a non-ionic polymer containing lactam which is polyvinyl pyrrolidone in an amount from approximately 0.015% to approximately 6% by weight, wherein said non-ionic polymer containing lactam interacts with said peroxides and said peracids by forming complexes; and wherein said non-ionic polymer containing lactam forms associations and adducts with said anionic photoreactive surfactant containing phosphate ester, said associations and adducts providing additional reactive chemistry that enhances the microbiocidal efficacy of the compositions.

2. The composition of claim 1, wherein said peroxides comprise hydrogen peroxide.

3. The composition of claim 2 wherein said hydrogen peroxide concentration is between approximately 0.1% and approximately 10% by weight.

4. The composition of claim 2 wherein said hydrogen peroxide concentration is between approximately 0.1% and approximately 6% by weight.

5. The composition of claim 2 wherein said hydrogen peroxide concentration is approximately 4% by weight.

6. The composition of claim 1, wherein said peracids comprise peroxyacetic acid.

7. The composition of claim 6, wherein said peroxyacid concentration is in the range of approximately 50 ppm to approximately 3% by weight.

8. The composition of claim 6, wherein said peroxyacetic acid concentration is in the range of approximately 0.2% by weight.

9. The composition of claim 1, wherein said equilibrium reaction products comprise acetic acid.

10. The composition of claim 1, wherein said non-ionic polymer containing lactam concentration is in the range from approximately 0.1% to approximately 3% by weight.

11. The composition of claim 1 wherein said non-ionic polymer containing lactam concentration is approximately 0.1% by weight.

12. The composition of claim 1, wherein said anionic photoreactive surfactant containing phosphate ester comprises a mixture comprising ethoxylated phosphate mono- and diesters.

13. The composition of claim 1, wherein said anionic photoreactive surfactant containing phosphate ester comprises a mixture comprising phosphate mono- and diesters of nonyl phenol ethoxylate.

14. The composition of claim 1, wherein said anionic photoreactive surfactant containing phosphate ester comprises a mixture comprising phosphate mono- and diesters of tri-decyl alcohol ethoxylate.

15. The composition of claim 1, wherein said anionic photoreactive surfactant containing phosphate ester and said non-ionic polymer containing lactam assist a multifunctional photo-enhanced microbicidal action of said composition.

16. The composition of claim 1, wherein said non-ionic polymer containing lactam interacts with said peroxides and said peracids further by formation of adducts.

17. The composition of claim 1 wherein said composition is in the form of a concentrate.

18. A method of decontaminating a surface, comprising the step of applying a solution comprising the composition of claim 1 to said surface.

19. The method of claim 18, further comprising exposing said surface to light.

20. The method of claim 19, wherein said light comprises ultraviolet light.

21. The method of claim 19, wherein said light comprises ultraviolet light with wavelengths in the range of approximately 170 nm to approximately 400 nm.

22. The method of claim 19, wherein said light comprises ultraviolet light with wavelengths in the range of approximately 210 nm to approximately 310 nm.

23. A method of decontaminating smooth or porous surfaces comprising applying the composition of claim 1 to said surface.

24. A method of killing bacterial spores comprising:
    applying the composition of claim 1 to said spores; and
    exposing said spores to light substantially lacking in ultraviolet light content.

25. An antimicrobial composition comprising:
    4% by weight hydrogen peroxide;
    2000 ppm peroxyacetic acid;
    an equilibrium quantity of acetic acid;
    0.1% to 1% by weight of an non-ionic polymer containing lactam which is polyvinyl pyrrolidone, wherein said non-ionic polymer containing lactam interacts with said hydrogen peroxide and said peroxyacetic acid; and
    0.05% to 0.5% by weight of an anionic photoreactive surfactant comprising a phosphate ester comprising a hydrophilic polyoxyethylene chain having a range of PEO-3 to PEO-9 and an R-terminal group selected from the group consisting of a lipophilic alkyl chain having a range of C9 to C13 and an nonylphenol, wherein said non-ionic polymer containing lactam forms associations and adducts with said anionic photoreactive surfactant containing phosphate ester, said associations and adducts providing additional reactive chemistry that enhances the microbiocidal efficacy of the composition.

26. The composition of claim 25 wherein said anionic photoreactive surfactant containing phosphate ester comprises a mixture of comprising ethoxylated phosphate mono- and diesters.

27. The composition of claim 25 wherein said anionic photoreactive surfactant containing phosphate ester comprises a mixture comprising phosphate mono- and diesters of nonylphenol ethoxylate.

28. A binary microbicidal and decontaminant composition comprising:
    a first part comprising a stabilized solution comprising hydrogen peroxide, acetic acid, and peroxyacetic acid; and
    a second part comprising an anionic photoreactive surfactant comprising a phosphate ester comprising a hydrophilic polyoxyethylene chain having a range of PEO-3 to PEO-9 and an R-terminal group selected from the group consisting of a lipophilic alkyl chain having a range of C9 to C13 and an nonylphenol, and a non-ionic polymer containing lactam, which is polyvinyl pyrrolidone said photoreactive surfactant containing phosphate ester;
    wherein said first part and said second part when mixed form a microbicidal solution having an amount of polyvinyl pyrrolidone from approximately 0.015% to approximately 6% by weight, such that said non-ionic polymer interacts with said hydrogen peroxide and said peroxyacetic acid, and wherein said polymer forms associations and adducts with said surfactant, said associations and adducts providing additional reactive chemistry that enhances the microbiocidal efficacy of the composition.

29. The composition of claim 28 wherein said second part further comprises minors.

30. The composition of claim 28 wherein said microbicidal solution further comprises a balance of water.

31. The composition as claimed in claim 28 wherein at least one of
said first part and said second part are in the form of a concentrate.

32. The composition of claim 25 wherein said antimicrobial composition is also a sterilant.

* * * * *